(12) United States Patent
La Thangue et al.

(10) Patent No.: US 6,376,215 B1
(45) Date of Patent: Apr. 23, 2002

(54) JMY, A CO-ACTIVATOR FOR P300/CBP, NUCLEIC ACID ENCODING JMY AND USES THEREOF

(75) Inventors: Nicholas Barrie La Thangue, Ennelly (GB); Noriko Shikama, Chiba (JP)

(73) Assignee: The University Court of the University of Glasgow, Glasgow (GB)

(*) Notice: Subject to any disclaimer, the term of this patent is extended or adjusted under 35 U.S.C. 154(b) by 0 days.

(21) Appl. No.: 09/311,236

(22) Filed: May 13, 1999

Related U.S. Application Data

(63) Continuation of application No. PCT/GB98/03152, filed on Oct. 21, 1998.

(30) Foreign Application Priority Data

Oct. 21, 1997 (GB) .............................................. 9722238
Aug. 20, 1998 (GB) .............................................. 9818235

(51) Int. Cl.$^7$ ......................... C12N 15/12; C12N 15/63; C12N 5/06; C07H 21/04
(52) U.S. Cl. ................... 435/69.1; 435/320.1; 435/325; 536/23.5
(58) Field of Search ...................... 536/23.5; 435/320.1, 435/325, 69.1

(56) References Cited

FOREIGN PATENT DOCUMENTS

| | | |
|---|---|---|
| EP | 0 120 694 A2 | 10/1984 |
| EP | 0 125 023 A1 | 11/1984 |
| EP | 0 184 187 A2 | 6/1986 |
| EP | 0 239 400 A2 | 9/1987 |
| WO | WO 89/03891 | 5/1989 |
| WO | WO 90/13667 | 11/1990 |
| WO | WO 92/01047 | 1/1992 |
| WO | WO 94/10307 | 5/1994 |
| WO | WO 94/21787 | 9/1994 |
| WO | WO 95/14091 | 5/1995 |
| WO | WO 96/15243 | 5/1996 |
| WO | WO 96/25494 | 8/1996 |
| WO | WO 97/43647 | 11/1997 |
| WO | WO 98/03652 | 1/1998 |

OTHER PUBLICATIONS

Macke, J. et al. 26f7 Human retina cDNA randomly primed sublibrary Homo sapiens cDNA, mRNA sequence. EST. Accession No. W26371. May 5, 1996.*
Marra, M. et al. mm43e08.r1 Stratagene mouse melanoma (#937312) Mus musculus cDNA clone IMAGE:524294 5', mRNA sequence. EST. Accession No. AA065698. Feb. 6, 1997.*
Mikayama T. Molecular cloning and functional expression of a cDNA encoding glycosylation–inhibiting factor. Proc. Natl. Acad. Sci. USA vol. 90, pp. 10056–10060, 1993.*
Voet et al. Biochemistry. 1990. John Wiley & Sons, Inc.. pp. 126–128 and 228–234.*
Futterer, A. et al. Molecular Cloning and Charaterization of Human Kinectin. Molecular Biology of the Cell. vol. 6; pp. 161–170, 1995.*
Kruppa, G. et al. Kinectin 1–human. PIR Accession. No. S32763. Jan. 6, 1995.*
Fields and Song, *Nature*, 340:245–246 (1989).
Kaelin et al., *Cell*, 70:351–364 (1992).
Xiong et al., *Cell*, 65(4):691–699 (1991).
Arany et al., A family of transcription adaptor proteins targeted by the E1A oncoprotein, *Nature*, 374:81–84, 1995.
Armitage et al., "Molecular and biological characterization of a murine ligand for CD40," *Nature*, 357:80–82, 1992.
Avantaggiati et al., "SV40 large T antigen and adenovirus E1a oncoproteins interact with distinct isoforms of the transcriptional co–activator, p300," *The EMBO Journal*, 15(9):2236–2248, 1996.
Bannister et al., "The CBP co–activator is a histone acetyl-transferase," *Nature*, 384:841–643, 1996.
Beijersbergen et al., E2F–4, a new member of the E2F gene family . . . *Genes and Develop.*, 8:2680–2690, 1994.
Blömer et al., "Applications of gene therapy of the CNS," *Human Molecular Genetics*, 5:1397–1404, 1996.
Borrow et al., "The translocation t(8;16) (p11;p13) of acute myeloid leukaemia fuses a putative acetyltransferase . . . ," *Nature Genetics*, 14:33–41, 1996.
Buck et al., "Molecular and functional characterisation of E2F–5, . . . " *Oncogene*, 11:31–38, 1995.
Capecchi, "Altering the Genome by Homologous Recombination," *Science*, 244:1288–1292, 1989.
Chakravarti et al, "Role of CBP/P300 in nuclear receptor signalling," *Nature*, 383:99–102, 1996.
Chen et al., "Nuclear Receptor Coactivator ACTR Is a Novel Histone Acetyltransferase . . . ," *Cell*, 90:569–580, 1997.
Crook et al., "Transcriptional Activation by p53 Correlates with Suppression of Growth but Not Transformation," *Cell*, 79:817–827, 1994.
Crooke, "Therapeutic Applications of Oligonucleotides," *Annu., Rev. Pharmacol. Toxicol.*, 32:329–376, 1992.
Eckner et al., "Molecular cloning and functional analysis . . . ," *Genes & Develop.*, 8:869–884, 1994.
El Deiry et al., "WAF1, a Potential Mediator of p53 Tumor Suppression," *Cell*, 75:817–825, 1993.
Gibson and Shillitoe, "Ribozymes, Their functions and Strategies for Their Use" *Molecular Biotechnology*, 7:125–137, 1997.
Girling et al., "A new component of the transcription factor DRTF1/E2F," *Nature*, 362:83–87, 1993.

(List continued on next page.)

Primary Examiner—Prema Mertz
Assistant Examiner—Joseph F. Murphy
(74) Attorney, Agent, or Firm—Banner & Witcof, Ltd.

(57) ABSTRACT

The invention provides an isolated nucleic acid (SEQ ID NO:1) encoding a novel protein, JMY, which is found to be a co-activator of p300/CBP. The invention also provides JMY polypeptides and antibodies thereto, as well as assays for modulators of the cell cycle which target the interaction of JMY with transcription factors such as E2F, ER or TBP.

6 Claims, 4 Drawing Sheets

OTHER PUBLICATIONS

Glass et al., "Nuclear receptor coactivators," *Cell regulation*, pp. 222–232, 1997.

Greene et al, "Sequence and Expression of Human Estrogen Receptor Complementary DNA," *Science* 231:1150–1154, 1986.

Gu and Roeder, "Activation of p53 Sequence–Specific DNA Binding by Acetylation of the p53 C–Terminal Domain," *Cell*, 90:595–606, 1997.

Gu et al., Synergistic activation of transcription by CBP and p53, *Nature*, 387:819–822, 1997.

Guo et al., "Fluorescence Resonance Energy Transfer Reveals Interleukin (IL)–1–dependent Aggregation . . . ," *J. Bio. Chem.*, 270(46):27562–27568, 1995.

Hanstein et al., "p300 is a component of an estrogen receptor coactivator complex," *Proc. Natl. Acad. Sci. USA*, 93:11540–11545, 1996.

Hasty et al., "Introduction of a subtle mutation into the Hox–2.6 locus in embryonic stem cells," *Nature*, 350:243–246, 1991.

Helin et al., "A cDNA Encoding a pRB–Binding Protein with Properties of the Transcription Factor E2F," *Cell*, 70:337–350, 1992.

Hijmans et al., "E2F–5, a New E2F Family Member that Interacts with p130 In Vivo," *Mol. & Cell., Biol.*, 15(6):3082–3089, 1995.

Ivey–Hoyle et al., "Cloning and Characterization of E2F–2, . . . ," *Mol. & Cell., Biol.*, 13(12):7802–7812, 1993.

Ko and Prives, "p53: puzzle and paradigm," *Genes & Develop.*, 10:1054–1072, 1996.

Lamb and Crawford, "Characterization . . . Human p53 Gene," *Mol. & Cell. Biol.*, 6(5):1379–1385, 1986.

Lees et al., "The Retinoblastoma Protein Binds to a Family of E2F Transcription Factors," *Mol. & Cell., Biol.*, 13(12):7813–7825, 1993.

Li et al., "RAC3, a steroid/nuclear receptor–associated coactivator that is related to SRC–1 and TIF2," *Proc. Natl. Acad., USA*, 94:8479–8484, 1997.

Lill et al., "Binding and modulation of p53 by p300/CBP coactivators," *Nature*, 387:823–827, 1997.

Lundblad et al., "Adenoviral E1A–associated protein p300 as a functional homologue of the transcriptional co–activator CBP," *Nature*, 374:85–88, 1995.

Marra et al., "The WashU–HHMI Mouse EST Project," sequence, XP–002096738,EMBL Database, acccession No. AA065698.

Matlashewski et al., "Isolation and characterization of a human p53 cDNA clone: expression of the human p53 gene," *Human p53 cDNA*, pp. 3257–3262, IRL Press Ltd., Oxford, England, 1984.

Miyashita and Reed, "Tumor Suppressor p53 Is a Direct Transcriptional Activator of the Human bax Gene," *Cell*, 80:293–299, 1995.

Muraoka et al., "p300 gene alterations in colorectal and gastric carcinomas," *Oncogene*, 12:1565–1569, 1996.

Nathans, "Adult Human Retina cDNA," sequence, XP–002096739,EMBL Database, accession No. W26371.

Neuman et al., "Cyclin D1 Stimulation of Estrogen Receptor Transcriptional Activity Independent of cdk4†," *Mol. & Cell. Biol.*, 17(9):5338–5347, 1997.

Ogryzko et al., "The Transcriptional Coactivators p300 and CBP Are Histone Acetyltransferases," *Cell*, 87:953–959, 1996.

Oñate et al., "Sequence and Characterization of a Coactivator for the Steroid Hormone Receptor Superfamily," *Science*, 270:1354–1357, 1995.

Perkins et al., "Regulation of NF–κB by Cyclin–Dependent Kinases Associated with the p300 Coactivator," *Science*, 275:523–527, 1997.

Puri et al., "p300 is required for MyoD–dependent cell cycle . . . ," *J. EMBO*, 16(2):369–383, 1997.

Sabbatini et al., "Essential role for p53–mediated transcription in E1 A–induced apoptosis," *Genes & Develop.*, 9:2184–2192, 1995.

Sadovsky et al., "Transcriptional Activators Differ in Their Responses to Overexpression of TATA–Box–Binding Protein," *Mol. & Cell. Biol.*, 15(3):1554–1563, 1995.

Shikama et al., "The p330/CBP family: . . . ," *Cell Biol.*, 7:230–236, 1997.

Sorensen et al., "Functional Interaction between DP–1 and p53," *Mol. & Cell. Biol.*, 16(10):5888–5895, 1996.

Torchia et al., "The transcriptional co–activator p/CIP binds CBP and mediates nuclear–receptor function," *Nature*, 387:677–684, 1997.

Tsien et al., "Subregion– and Cell Type–Restricted Gene Knockout in Mouse Brain," *Cell*, 87:1317–1326, 1996.

Uhlman and Peyman, "Antisense Oligonucleotides," *Chemical Reviews*, 90(4):545–584, 1990.

Valancius and Smithies, "Testing an 'In–Out' Targeting Procedure for Making Subtle Genomic Modifications in Mouse Embryonic Stem Cells," *Mol. & Cell. Biol.*, 11(3):1402–1408, 1991.

Vojtek et al., "Mammalian Ras Interacts Directly with the Serine/Threonine Kinase Raf," *Cell*, 74:205–214, 1993.

Walther and Stein, "Targeted Vectors for Gene Therapy of Cancer and Retroviral Infections," *Mol. Biotech.*, 6:267–286, 1996.

Yang et al., "A p300/CBP–associated factor that competes with the adenoviral oncoprotein E1A," *Nature*, 382:319–324, 1996.

Zamecnik and Stephenson, "Inhibition of Rous sarcoma virus replication and cell transformation by a specific oligodeoxynucleotide," *Proc. Natl. Acad. Sci., USA*, 75(1):280–284, 1978.

Zwijsen et al., "CDK–Independent Activation of Estrogen Receptor by Cyclin D1," *Cell*, 88:405–415, 1997.

\* cited by examiner

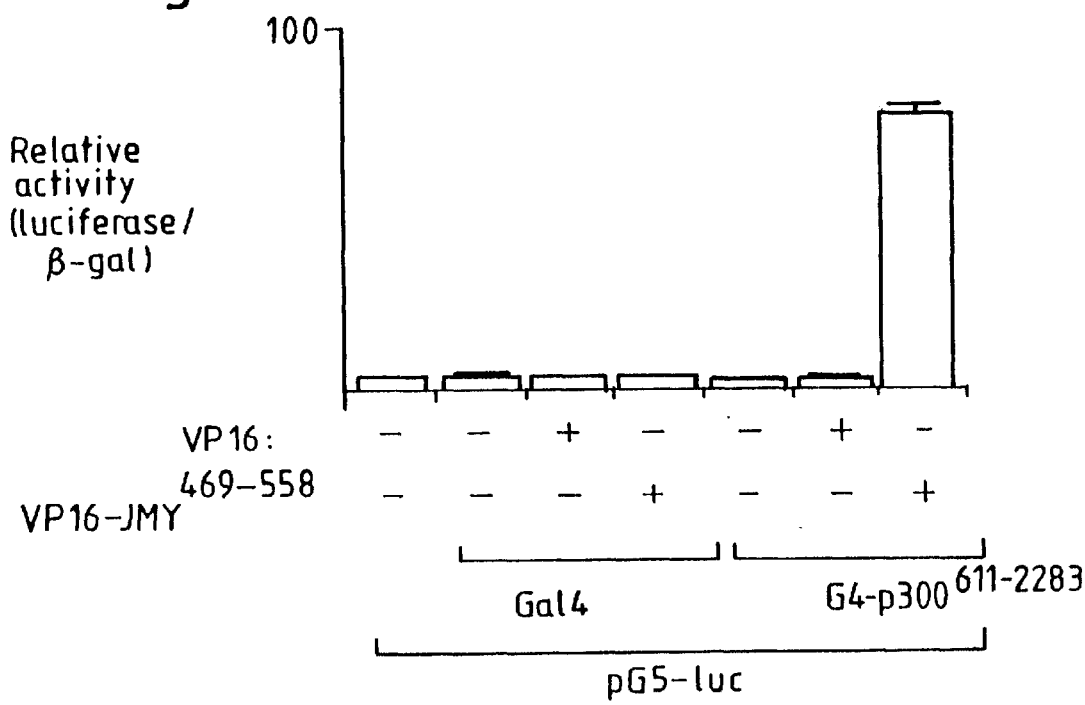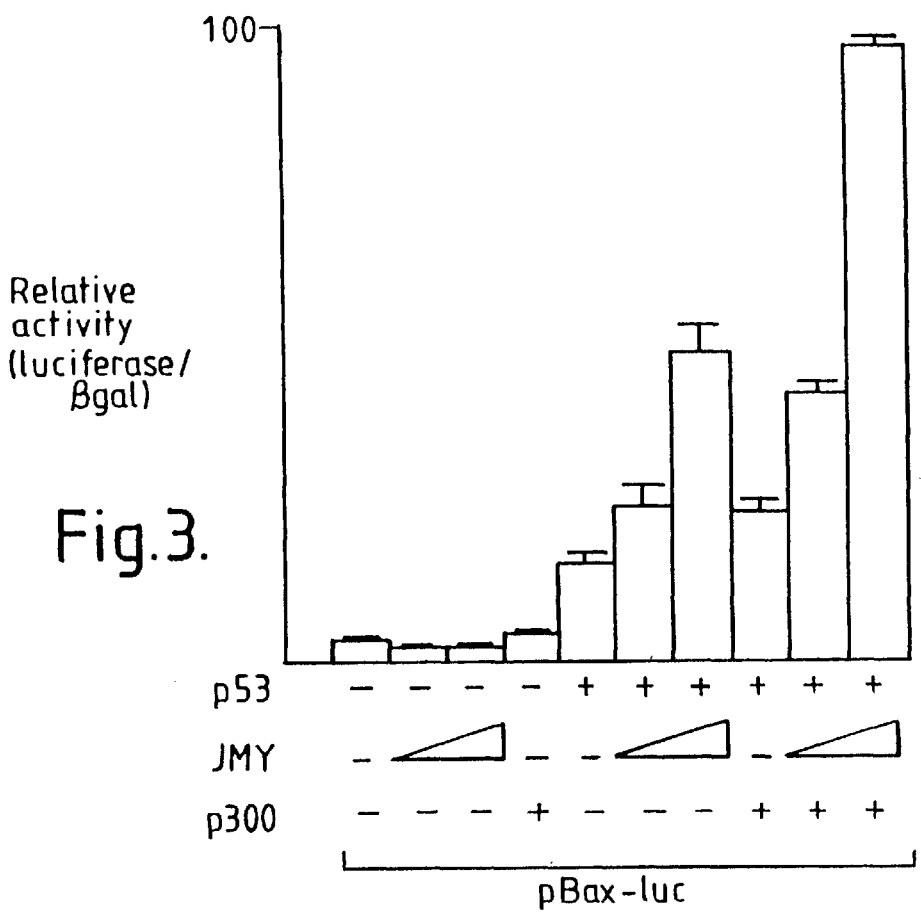

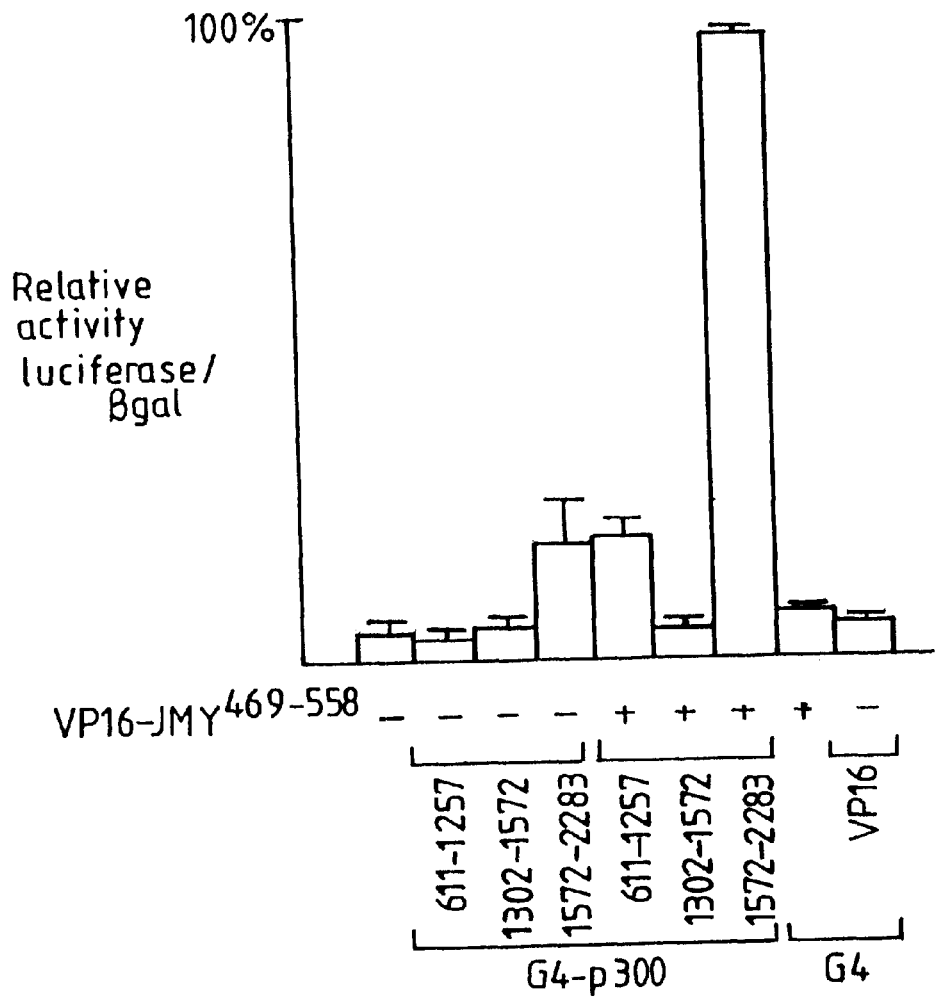
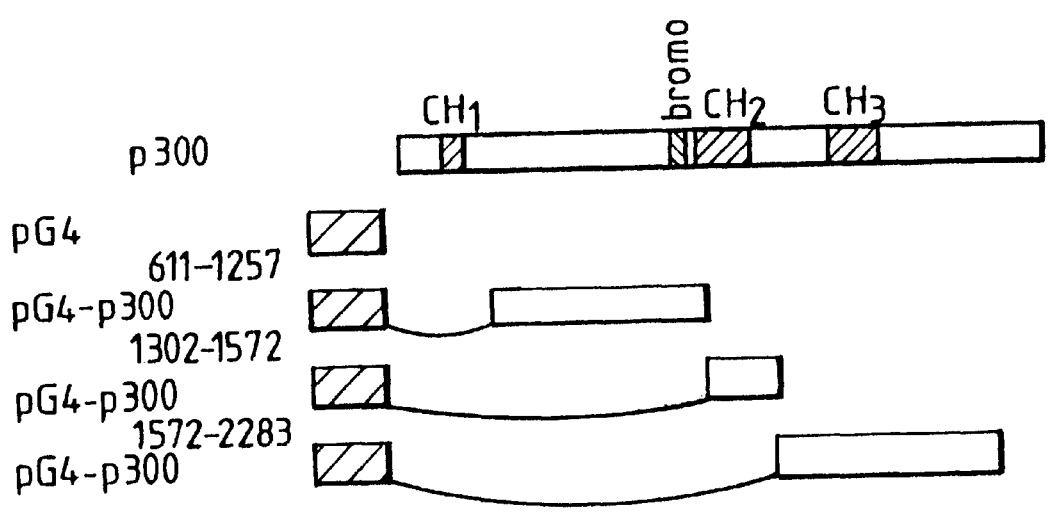
Fig.2.

SEQUENCE LISTING

<160> NUMBER OF SEQ ID NOS: 3

<210> SEQ ID NO 1
<211> LENGTH: 3574
<212> TYPE: DNA
<213> ORGANISM: Mus sp.

<400> SEQUENCE: 1

| | | | | | | |
|---|---|---|---|---|---|---|
| agccggtggg | tgagcggccg | gcgcgctaag | atggctgcag | gcgccccgca | agggtgagct | 60 |
| gggggcgcgg | ccaccgcgga | gactcggccg | ggcgggcgac | ccccctcgcc | gggcaccgga | 120 |
| gctaccatgt | cgttcgcgct | ggaggagaca | ctcgagtccg | actgggtggc | ggtgcggccc | 180 |
| cacgtattcg | acgagcgcga | gaagcacaag | tttgtgttca | ttgtggcctg | gaacgagatc | 240 |
| gaaggcaagt | ttgctataac | ctgtcacaac | cggacggccc | agagacagag | gagcggttcc | 300 |
| cgggaacagg | cggggacgcc | cgcgtctgat | gggagtcgcg | gtccgggcag | ccccgcggcc | 360 |
| aggggtcggt | cagaggccgc | tgcctctgct | acagcagcgc | tccggagtcc | cgggccacgg | 420 |
| aaaagccagg | cctgggccga | gggcggctct | ccgcgcagcg | cgcgcagcct | gaaggggat | 480 |
| cctcctcggg | gtcccgcggg | cagaggaccg | gagagtcctc | tccgtagccc | cgcgcgggct | 540 |
| aaggccagcc | cgctccgcag | aagcgccgaa | tcccgagatg | cgatcgccag | tgccacgcca | 600 |
| gtcccgccgg | cgcccccggt | gccccggtg | tcgtcggtgc | gggtggtgag | tgcctccggg | 660 |
| gcggtctccg | aggagatcga | ggttctgaa | atggtgaggg | aggacgaggc | gccacagccg | 720 |
| ctcccggact | cggagcagcc | gccgtctgcc | gcggagctgg | agtcttcggc | cgaagaatgc | 780 |
| agctgggccg | ggcttttctc | cttccaggat | ctgcgagccg | tgcatcagca | gctgtgctcg | 840 |
| gtaaactccc | agctggagcc | gtgtctgccg | gtgttccccg | aagagccgtc | aggcatgtgg | 900 |
| acggtgctgt | ttggggcgc | ccccgagatg | accgagcagg | agatcgacgc | tctatgttac | 960 |
| caactccagg | tctacctggg | ccacggcctg | gacacgtgtg | gctggaagat | cctttctcag | 1020 |
| gttcttttca | ccgagacgga | tgatccggag | gagtattacg | aaagcctcag | cgagctgcgg | 1080 |
| cagaagggct | atgaagaggt | gcttcagcgg | gccaggaggc | gcatccagga | gctcttggac | 1140 |
| aagcacaaga | ctatagaaag | catggtagag | cttttggact | tgtatcagat | ggaggatgaa | 1200 |
| gcctacagca | gccttgcaga | ggccacaact | gaactctacc | agtatttact | tcagccattc | 1260 |
| cgagacatgc | gagaactggc | catgctacga | agacagcaga | tcaagatttc | catggagaat | 1320 |
| gattatttgg | gccctcgaag | aattgagagt | ctacagaaag | aagatgctga | ctggcagcgg | 1380 |
| aaagctcaca | tggctgtttt | gtctattcag | gatctcaccg | tcaaatattt | tgaaataaca | 1440 |
| gcaaaagctc | agaaagctgt | gtatgatcgg | atgcgagcag | atcagaagaa | atttggcaaa | 1500 |
| gcatcgtggg | cagcagctgc | tgagcgaatg | gaaaaactcc | agtatgcagt | ttctaaagag | 1560 |
| actttgcaga | tgatgagagc | taaagaaatt | tgtctggaac | agaagaaaca | tgcactaaaa | 1620 |
| gaagagatgc | aaagcttaca | gggtggtaca | gaagctatag | ctcgattgga | tcagctggaa | 1680 |
| tctgactact | atgatctgca | acttcagttg | tatgaagtac | agtttgaaat | cttgaagtgt | 1740 |
| gaagagttgt | tattaactgc | acagctggag | agcatcaaga | gacttatatc | agaaaagaga | 1800 |
| gatgaagtgg | tgtactacga | cacttacgaa | agcatggagg | ccatgctgga | gaaggaagag | 1860 |
| atggcagcgt | ctgtgcacgc | ccagaggaa | gagctacaga | aactgcagca | gaaggcacgc | 1920 |
| cagctggaag | caagaagggg | ccgtgtctca | gccaagaaag | cctacctcag | aaataaaaaa | 1980 |
| gaaatttgca | ttgcaaaaca | ccatgagaag | ttccagcagc | gttttcagag | tgaagatgaa | 2040 |

```
tatagagccc atcatacaat acaaataaag agagacaaat tgcatgatga agaggaaaga    2100
aaaagtgcct gggttagcca agagagacag aggacactgg atagacttcg aacatttaag    2160
cagaggtacc ccgggcaagt catccttaag tcgaccagat tacgagtggc gcattcaaga    2220
agaaaaagca cagcaagccc tgtgccctgt gaggagcagt gtcactctct gccaacagtg    2280
ctgcaggggc aggagaagac agaggtggga ggaggaggaa gccagcttgg gccttcacag    2340
acagcagaac cccagagcct tgtccaactt gaagacactt catcagaaca acttgaatcc    2400
acctcattac ctcctcgtgc tgtcgtcagc tctgaactgc ctcctccaca gtcagctcca    2460
ctgttgacta gtattgaccc caaaccgtgt tctgttacta tagatcctct cccacccccct   2520
cttcctccaa cacctccccc tccccacccc caccccccac ctccacccccc accctgcct    2580
gttgcaaagg acaatgggc ctccaccact gcagagacac tggagaaaga tgcacttagg    2640
acggagggca atgagaggag catcccaaag tcggccagtg ccccgcagc acacctcttt     2700
gatagcagcc agctggtcag cgcacggaaa aagctcagaa agactgtgga agggctgcag    2760
aggaggagag tgagttcacc catggatgaa gtgttagcat ccttgaagcg tggtagcttt    2820
catctgaaaa aggttgaaca gcggactctg cctcctttc ctgatgaaga tgatagtaat      2880
aatattttgg cgcagataag gaaagggta agttgaaga aggttcagaa ggaagttttg      2940
agagaatcct tcacacttct gcctgatacc gacccttga cacggagtat ccacgaagct      3000
ctaagaagaa tcaaagaagc gtccccagag tcagaggatg aggaagaggc tttgccgtgc    3060
acagactggg agaactagca ggtgacttaa gagagaagaa aaatacccat ggatgaagac    3120
tggctctggt tcctttgggg aaaaaatcta agctcttggt cccacaattg gattccatta    3180
tgtcctgagt atattgacaa agtggtttga aaaggaagc acaaacggga ggttactact     3240
gtccagtccc tctcattgat agtgcaatgt tcccgactgc agagagaaca gcctcctgg     3300
agacggctgt tccttcccca ccctcctcc ccatctgccc aatcataatc tcatagtggc     3360
cagtcccatt gctatgaatt ggaagaacac tgggttggca gaggtctgct gtacgagcta    3420
ctttgggatt catctttcag tgaactgaga agatctgtgc tgaagcacag ccgcttccat    3480
gtcagcttgt agagacagag agacatgcta cagaagacat tgatcaaggt agttatggtc   3540
aggaattaaa aaaaaccat gaaatgcaaa aaaa                                 3574
```

<210> SEQ ID NO 2
<211> LENGTH: 983
<212> TYPE: PRT
<213> ORGANISM: Mus sp.

<400> SEQUENCE: 2

```
Met Ser Phe Ala Leu Glu Glu Thr Leu Glu Ser Asp Trp Val Ala Val
  1               5                  10                  15

Arg Pro His Val Phe Asp Glu Arg Glu Lys His Lys Phe Val Phe Ile
                 20                  25                  30

Val Ala Trp Asn Glu Ile Glu Gly Lys Phe Ala Ile Thr Cys His Asn
             35                  40                  45

Arg Thr Ala Gln Arg Gln Arg Ser Gly Ser Arg Glu Gln Ala Gly Thr
         50                  55                  60

Pro Ala Ser Asp Gly Ser Arg Gly Pro Gly Ser Pro Ala Ala Arg Gly
     65                  70                  75                  80

Arg Ser Glu Ala Ala Ala Ser Ala Thr Ala Ala Leu Arg Ser Pro Gly
                 85                  90                  95
```

```
Pro Arg Lys Ser Gln Ala Trp Ala Glu Gly Gly Ser Pro Arg Ser Ala
            100                 105                 110

Arg Ser Leu Lys Gly Asp Pro Pro Arg Gly Pro Ala Gly Arg Gly Pro
            115                 120                 125

Glu Ser Pro Leu Arg Ser Pro Ala Arg Ala Lys Ala Ser Pro Leu Arg
            130                 135                 140

Arg Ser Ala Glu Ser Arg Asp Ala Ile Ala Ser Ala Thr Pro Val Pro
145                 150                 155                 160

Pro Ala Pro Pro Val Pro Pro Val Ser Val Arg Val Val Ser Ala
                    165                 170                 175

Ser Gly Ala Val Ser Glu Glu Ile Glu Val Leu Glu Met Val Arg Glu
            180                 185                 190

Asp Glu Ala Pro Gln Pro Leu Pro Asp Ser Glu Gln Pro Ser Ala
            195                 200                 205

Ala Glu Leu Glu Ser Ser Ala Glu Glu Cys Ser Trp Ala Gly Leu Phe
            210                 215                 220

Ser Phe Gln Asp Leu Arg Ala Val His Gln Leu Cys Ser Val Asn
225                 230                 235                 240

Ser Gln Leu Glu Pro Cys Leu Pro Val Phe Pro Glu Pro Ser Gly
                    245                 250                 255

Met Trp Thr Val Leu Phe Gly Gly Ala Pro Glu Met Thr Glu Gln Glu
            260                 265                 270

Ile Asp Ala Leu Cys Tyr Gln Leu Gln Val Tyr Leu Gly His Gly Leu
            275                 280                 285

Asp Thr Cys Gly Trp Lys Ile Leu Ser Gln Val Leu Phe Thr Glu Thr
            290                 295                 300

Asp Asp Pro Glu Glu Tyr Tyr Glu Ser Leu Ser Glu Leu Arg Gln Lys
305                 310                 315                 320

Gly Tyr Glu Glu Val Leu Gln Arg Ala Arg Arg Ile Gln Glu Leu
                    325                 330                 335

Leu Asp Lys His Lys Thr Ile Glu Ser Met Val Glu Leu Leu Asp Leu
            340                 345                 350

Tyr Gln Met Glu Asp Glu Ala Tyr Ser Ser Leu Ala Glu Ala Thr Thr
            355                 360                 365

Glu Leu Tyr Gln Tyr Leu Leu Gln Pro Phe Arg Asp Met Arg Glu Leu
            370                 375                 380

Ala Met Leu Arg Arg Gln Gln Ile Lys Ile Ser Met Glu Asn Asp Tyr
385                 390                 395                 400

Leu Gly Pro Arg Arg Ile Glu Ser Leu Gln Lys Glu Asp Ala Asp Trp
                    405                 410                 415

Gln Arg Lys Ala His Met Ala Val Leu Ser Ile Gln Asp Leu Thr Val
            420                 425                 430

Lys Tyr Phe Glu Ile Thr Ala Lys Ala Gln Lys Ala Val Tyr Asp Arg
            435                 440                 445

Met Arg Ala Asp Gln Lys Lys Phe Gly Lys Ala Ser Trp Ala Ala Ala
            450                 455                 460

Ala Glu Arg Met Glu Lys Leu Gln Tyr Ala Val Ser Lys Glu Thr Leu
465                 470                 475                 480

Gln Met Met Arg Ala Lys Glu Ile Cys Leu Glu Gln Lys Lys His Ala
                    485                 490                 495

Leu Lys Glu Glu Met Gln Ser Leu Gln Gly Gly Thr Glu Ala Ile Ala
            500                 505                 510

Arg Leu Asp Gln Leu Glu Ser Asp Tyr Tyr Asp Leu Gln Leu Gln Leu
```

-continued

```
            515                 520                 525
    Tyr Glu Val Gln Phe Glu Ile Leu Lys Cys Glu Glu Leu Leu Leu Thr
            530                 535                 540
    Ala Gln Leu Glu Ser Ile Lys Arg Leu Ile Ser Glu Lys Arg Asp Glu
    545                 550                 555                 560
    Val Val Tyr Tyr Asp Thr Tyr Glu Ser Met Glu Ala Met Leu Glu Lys
                        565                 570                 575
    Glu Glu Met Ala Ala Ser Val His Ala Gln Arg Glu Glu Leu Gln Lys
                    580                 585                 590
    Leu Gln Gln Lys Ala Arg Gln Leu Glu Ala Arg Arg Gly Arg Val Ser
                595                 600                 605
    Ala Lys Lys Ala Tyr Leu Arg Asn Lys Lys Glu Ile Cys Ile Ala Lys
    610                 615                 620
    His His Glu Lys Phe Gln Gln Arg Phe Gln Ser Glu Asp Glu Tyr Arg
    625                 630                 635                 640
    Ala His His Thr Ile Gln Ile Lys Arg Asp Lys Leu His Asp Glu Glu
                        645                 650                 655
    Glu Arg Lys Ser Ala Trp Val Ser Gln Glu Arg Gln Arg Thr Leu Asp
                    660                 665                 670
    Arg Leu Arg Thr Phe Lys Gln Arg Tyr Pro Gly Gln Val Ile Leu Lys
                675                 680                 685
    Ser Thr Arg Leu Arg Val Ala His Ser Arg Arg Lys Ser Thr Ala Ser
            690                 695                 700
    Pro Val Pro Cys Glu Glu Gln Cys His Ser Leu Pro Thr Val Leu Gln
    705                 710                 715                 720
    Gly Gln Glu Lys Thr Glu Val Gly Gly Gly Ser Gln Leu Gly Pro
                        725                 730                 735
    Ser Gln Thr Ala Glu Pro Gln Ser Leu Val Gln Leu Glu Asp Thr Ser
                    740                 745                 750
    Ser Glu Gln Leu Glu Ser Thr Ser Leu Pro Pro Arg Ala Val Val Ser
                755                 760                 765
    Ser Glu Leu Pro Pro Pro Gln Ser Ala Pro Leu Leu Thr Ser Ile Asp
            770                 775                 780
    Pro Lys Pro Cys Ser Val Thr Ile Asp Pro Leu Pro Pro Leu Pro
    785                 790                 795                 800
    Pro Thr Pro Pro Pro Pro Pro Pro Pro Pro Pro Pro Pro Pro Pro Pro
                        805                 810                 815
    Leu Pro Val Ala Lys Asp Asn Gly Ala Ser Thr Thr Ala Glu Thr Leu
                    820                 825                 830
    Glu Lys Asp Ala Leu Arg Thr Glu Gly Asn Glu Arg Ser Ile Pro Lys
                835                 840                 845
    Ser Ala Ser Ala Pro Ala Ala His Leu Phe Asp Ser Ser Gln Leu Val
            850                 855                 860
    Ser Ala Arg Lys Lys Leu Arg Lys Thr Val Glu Gly Leu Gln Arg Arg
    865                 870                 875                 880
    Arg Val Ser Ser Pro Met Asp Glu Val Leu Ala Ser Leu Lys Arg Gly
                        885                 890                 895
    Ser Phe His Leu Lys Lys Val Glu Gln Arg Thr Leu Pro Pro Phe Pro
                    900                 905                 910
    Asp Glu Asp Asp Ser Asn Asn Ile Leu Ala Gln Ile Arg Lys Gly Val
                915                 920                 925
    Lys Leu Lys Lys Val Gln Lys Glu Val Leu Arg Glu Ser Phe Thr Leu
            930                 935                 940
```

```
Leu Pro Asp Thr Asp Pro Leu Thr Arg Ser Ile His Glu Ala Leu Arg
945                 950                 955                 960

Arg Ile Lys Glu Ala Ser Pro Glu Ser Glu Asp Glu Glu Glu Ala Leu
                965                 970                 975

Pro Cys Thr Asp Trp Glu Asn
            980

<210> SEQ ID NO 3
<211> LENGTH: 10
<212> TYPE: PRT
<213> ORGANISM: Mus sp.

<400> SEQUENCE: 3

Glu Val Gln Phe Glu Ile Leu Lys Cys Glu
  1               5                  10
```

JMY, A CO-ACTIVATOR FOR P300/CBP, NUCLEIC ACID ENCODING JMY AND USES THEREOF

This application is a continuation of PCT/GB98/03152 filed Oct. 21, 1998, now WO 9920752 issued Aug. 9, 2000, and United Kingdom Patent Application 9722238.4 filed Oct. 21, 1997 and United Kingdom Patent Application 9818235.5 filed Aug. 20, 1998.

FIELD OF THE INVENTION

The present invention relates to a novel gene which encodes a product which functions as a transcriptional co-activator.

BACKGROUND OF THE INVENTION

By regulating the transcriptional activity of a wide variety of transcription factors, the p300/CBP family of co-activators allow diverse signals to be integrated and co-ordinated with gene expression. Significantly, p300/CBP has been implicated as a critical regulator of distinct cellular pathways, such as those leading to differentiation, cell cycle arrest and apoptosis. The molecular mechanisms that enable these processes remain unclear, although the associated histone acetyltransferase and kinase activities are likely to play an important role.

SUMMARY OF THE INVENTION

We have used a two-hybrid assay system to identify a protein which interacts with p300/CBP. The protein, which we have called JMY, has a predicted molecular weight of 110kD and lacks significant similarity to other proteins. The identification of this protein and its gene provides, inter alia, novel nucleic acids, polypeptides and related products, and novel assay methods useful in identifying novel regulators of the cell cycle.

The present invention thus provides an isolated polypeptide which comprises residues 1 to 983 of SEQ ID NO. 2 or a polypeptide having at least 70% sequence identity to SEQ ID NO. 2. The invention further provides active portions and fragments which comprises an epitope of said polypeptide.

Unless otherwise specified below, such portions and fragments are also referred to as a polypeptide of the invention.

In another aspect, the invention provides an antibody capable of binding a polypeptide of the invention, such as a monoclonal antibody.

The invention also provides an isolated nucleic acid which encodes a polypeptide of the invention, including a nucleic acid which comprises or consists essentially of nucleotides 127 to 3075 of SEQ ID NO:1 or the complement thereof. The invention further provides a nucleic acid capable of selectively hybridizing to either strand of SEQ ID NO:1 such as a nucleic acid which has at least 70% homology to SEQ ID is NO:1. Fragments of such selectively hybridizing nucleic acids are also part of the invention. Also provided by the present invention are oligonucleotides which consist essentially of from 15 to 50 contiguous nucleotides of the nucleic acids mentioned above.

Unless specified to the contrary, all the above described nucleic acids are referred to as a "nucleic acid" or a "polynucleotide" of the invention.

The nucleic acids may be in the form of a vector, such as an expression vector wherein said nucleic acid is operably linked to a promoter heterologous to said nucleic acid. The promoter will be compatible with a desired host cell, and such host cells form a further aspect of the invention.

Nucleic acids encoding or associated with the JMY gene may be used in methods of detecting the presence or absence of said gene in a human or non-human mammalian subject, said method comprising;
(a) bringing a sample of nucleic acid from said subject into contact, under hybridizing conditions, with a polynucleotide of the invention; and
(b) determining whether said polynucleotide has been able to hybridize to a homologous sequence in said nucleic acid.

The method may be performed using a polynucleotide primer suitable for use in a polymerase chain reaction (PCR), and the determining may be performed in conjunction with a second primer using PCR such that a portion of the JMY gene is amplified.

In some instances, it the determining step may include determining the sequence of the JMY gene, when present, in the nucleic acid sample. As one alternative, restriction length fragment polymorphisms associated with the gene may be established and the assay performed with a sample which has been digested with a restriction enzyme. Another method of determining is via PCR length polymorphisms, for example through variation in the sizes of introns. Other specific means of determining hybridization are well known and routine in the art and may also be used.

The invention further provides immunological assays which comprise:
(a) bringing a body sample from said subject into contact, under binding conditions, with an antibody of the invention; and
(b) determining whether said antibody has been able to bind to a polypeptide in said sample.

We have also found that JMY is a potent coactivator of the estrogen receptor (ER). The invention thus provides assays for modulators which target the activation of the ER by JMY, optionally in the presence of p300/CBP. In another aspect, JMY also interacts with a number of transcription factors, including E2F, and these interactions provide further targets for modulators. Such modulators may influence the progression of the cell cycle.

As used herein, "comprise(s)" and "comprising" are to be interpreted as "include(s)" and "including".

The percentage homology (also referred to as identity) of DNA and amino acid sequences can be calculated using commercially available algorithms. The following programs (provided by the National Center for Biotechnology Information) may be used to determine homologies: BLAST, gapped BLAST and PSI-BLAST, which may be used with default parameters. The algorithm GAP (Genetics Computer Group, Madison, Wis.). GAP uses the Needleman and Wunsch algorithm to align two complete sequences that maximizes the number of matches and minimizes the number of gaps. Generally, the default parameters are used, with a gap creation penalty=12 and gap extension penalty=4. Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions.

Another method for determining the best overall match between a SEQ ID NO:1 or SEQ ID NO:2, or portions thereof, and a query sequence is the use of the FASTDB computer program based on the algorithm of Brutlag et al (Comp. App. Biosci., 6; 237–245 (1990)). The program provides a global sequence alignment. The result of said global sequence alignment is in percent identity. Suitable parameters used in a FASTDB search of a DNA sequence to calculate percent identity are:

Matrix=Unitary, k-tuple=4, Mismatch penalty=1, Joining Penalty=30, Randomization Group Length=0, Cutoff Score= 1, Gap Penalty=5, Gap Size Penalty=0.05, and Window Size=500 or query sequence length in nucleotide bases, whichever is shorter. Suitable parameters to calculate percent identity and similarity of an amino acid alignment are: Matrix=PAM 150, k-tuple=2, Mismatch Penalty=1, Joining Penalty=20, Randomization Group Length=0, Cutoff Score= 1, Gap Penalty=5, Gap Size Penalty=0.05, and Window Size=500 or query sequence length in nucleotide bases, whichever is shorter.

DESCRIPTION OF THE DRAWINGS

FIG. 1 shows the results of a mammalian two-hybrid assay confirming the interaction of p300 with JMY.

FIG. 2 shows that JMY interacts with two domains in p300.

FIG. 3 shows that JMY co-activates p53.

DETAILED DESCRIPTION OF THE INVENTION

A. Polypeotides

Figure 4A:
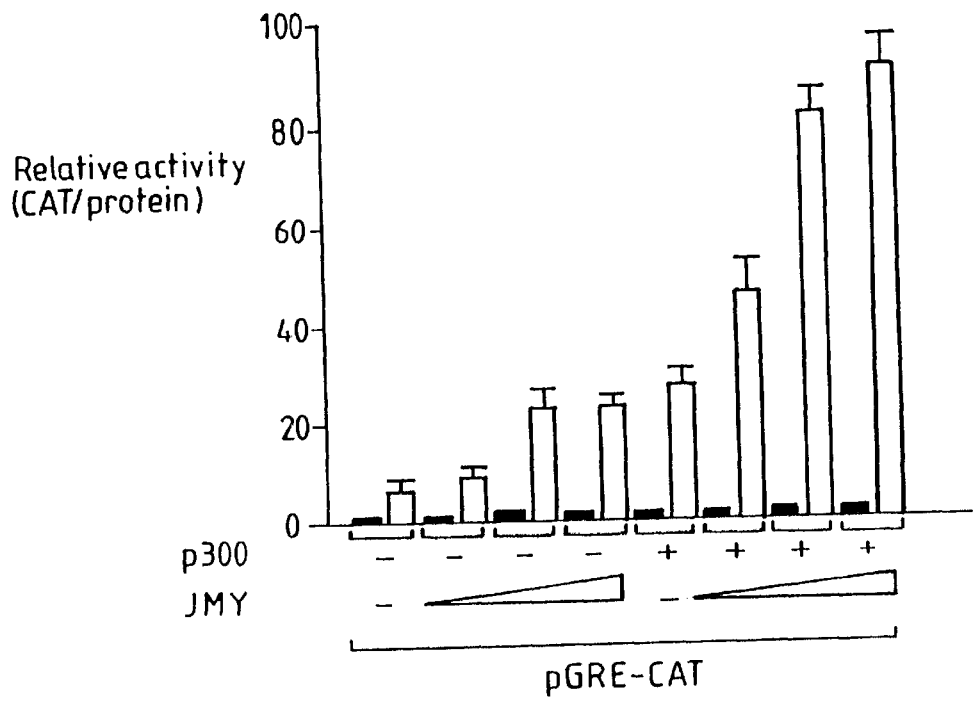
FIG. 4A co-expression of JMY and p300 provides transcriptional activation of the glucocorticoid receptor (GR).

Isolated polypeptides of the invention will be those as defined above in isolated form, free or substantially free of material with which it is naturally associated such as other polypeptides with which it is found in the cell. The polypeptides may of course be formulated with diluents or adjuvants and still for practical purposes be isolated—for example the polypeptides will normally be mixed with gelatin or other carriers if used to coat microtitre plates for use in immunoassays. The polypeptides may be glycosylated, either naturally or by systems of heterologous eukaryotic cells, or they may be (for example if produced by expression in a prokaryotic cell) unglycosylated. Polypeptides may be phosphorylated and/or acetylated.

A polypeptide of the invention may also be in a substantially purified form, in which case it will generally comprise the polypeptide in a preparation in which more than 90%, e.g. 95%, 98% or 99% of the polypeptide in the preparation is a polypeptide of the invention.

Polypeptides of the invention may be modified for example by the addition of histidine residues to assist their purification or by the addition of a signal sequence to promote their secretion from a cell.

Polypeptides which are amino acid sequence variants, alleles, derivatives or mutants are also provided by the present invention, such forms having at least 70% sequence identity, for example at least 80%, 90%, 95%, 98% or 99% sequence identity to SEQ ID NO. 2. A polypeptide which is a variant, allele, derivative or mutant may have an amino acid sequence which differs from that given in SEQ ID NO. 2 by one or more of addition, substitution, deletion and insertion of one or more (such as from 1 to 20, for example 2, 3, 4, or 5 to 10) amino acids.

Preferred such polypeptides include those which are encoded by the JMY gene of other mammals, particularly primates and most particularly man, as well as fragments of such polypeptides, such fragments being those as defined above. The primary sequence of the JMY protein will be substantially similar to that of SEQ ID NO:2 and may be determined by routine techniques available to those of skill in the art. In essence, such techniques comprise using polynucleotides of the present invention as probes to recover and to determine the sequence of the JMY gene in other species. A wide variety of techniques are available for this, for example PCR amplification and cloning of the gene using a suitable source of mRNA (e.g. from an embryo or an actively dividing differentiated or tumour cell), or by methods comprising obtaining a cDNA library from the mammal, e.g a cDNA library from one of the above-mentioned sources, probing said library with a polynucleotide of the invention under stringent conditions, and recovering a cDNA encoding all or part of the JMY protein of that mammal. Where a partial cDNA is obtained, the full length coding sequence may be determined by primer extension techniques.

An "active portion" of the polypeptides means a peptide which is less than said full length polypeptide, but which retains its essential biological activity. In particular, the active portion retains the ability to interact with p300/CBP. Suitable active portions thus include the central segment of SEQ ID NO:2 between about residues 470 and 550, for example between 450 to 550, 450 to 600, 400 to 550 and 400 to 600, as well as variants of such segments which retain the ability to interact with p300/CBP.

Active portions may also include those which are phosphorylated and/or acetylated, particularly in a cell-cycle specific manner.

Active portions may be used in methods of therapy including gene therapy.

An "inactive portion" of the polypeptides means a peptide which is still identifiable as a polypeptide of the invention but which through mutation is truncated or internally deleted. Examples of such polypeptides will include those which comprise at least 20, for example at least,30, 40, 50, 75 or 100 contiguous amino acids derived from SEQ ID NO:2, its variants including its species homologues.

Inactive portions may include at least one epitope to which antibodies are able to bind specifically.

Inactive portions may include fragments of the above-mentioned active portions which are capable of competing with the full length human or murine JMY protein for binding to p300. Preferably such fragments are those which are capable of antagonizing the formation of a JMY-p300 complex or JMY homodimerization, under conditions suitable for such complex formation or homodimerization to take place in the absence of such an inactive portion. Inactive portions also include dominant negative mutants of JMY.

A "fragment" means a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids. Fragments of the polypeptides comprise epitopes useful for raising antibodies to a portion of the amino acid sequences of SEQ ID NO. 2 or variants with at least 70% homology to SEQ ID NO. 2. Preferred epitopes are those to which antibodies are able to bind specifically, as defined below in section B.

As defined above, some fragments of the invention may be either active or inactive portions.

A polypeptide according to the present invention may be isolated and/or purified (e.g. using an antibody) for instance after production by expression from encoding nucleic acid (for which see below). Polypeptides according to the present invention may also be generated wholly or partly by chemical synthesis, for example in a step-wise manner. The isolated and/or purified polypeptide may be used in formulation of a composition, which may include at least one additional component, for example a pharmaceutical composition including a pharmaceutically acceptable excipient, vehicle or carrier. A composition including a polypeptide according to the invention may be used in prophylactic and/or therapeutic treatment as discussed below.

A polypeptide according to the present invention may be used as an immunogen or otherwise in obtaining specific antibodies. Antibodies are useful in purification and other manipulation of polypeptides and peptides, diagnostic screening and therapeutic contexts. This is discussed further below.

A polypeptide according to the present invention may be used in screening for molecules which affect or modulate its activity or function. Such molecules may be useful in a therapeutic (possibly including prophylactic) context.

A polypeptide of the invention may be labelled with a revealing label. The revealing label may be any suitable label which allows the polypeptide to be detected. Suitable labels include radioisotopes, e.g. $^{125}$I, enzymes, antibodies, polynucleotides and linkers such as biotin. Labelled polypeptides of the invention may be used in diagnostic procedures such as immunoassays in order to determine the amount of a polypeptide of the invention in a sample. Polypeptides or labelled polypeptides of the invention may also be used in serological or cell mediated immune assays for the detection of immune reactivity to said polypeptides in animals and humans using standard protocols.

A polypeptide or labelled polypeptide of the invention or fragment thereof may also be fixed to a solid phase, for example the surface of an immunoassay well or dipstick.

Such labelled and/or immobilized polypeptides may be packaged into kits in a suitable container along with suitable reagents, controls, instructions and the like.

Such polypeptides and kits may be used in methods of detection of antibodies to such polypeptides present in a sample or active portions or fragments thereof by immunoassay.

Immunoassay methods are well known in the art and will generally comprise:

(a) providing a polypeptide comprising an epitope bindable by an antibody against said protein;

(b) incubating a biological sample with said polypeptide under conditions which allow for the formation of an antibody-antigen complex; and (c) determining whether antibody-antigen complex comprising said polypeptide is formed.

The identification of the polypeptide expressed by the JMY gene enables assays to be developed to identify further cellular proteins with which the polypeptide is associated, in addition to p300/CBP. For example, polypeptides of the present invention may be required in a regulatory pathway in which their function is to interact with other factors which in turn promote or maintain essential cellular functions associated with cell cycle control. The polypeptides of the present invention may be used in two-hybrid assays to determine cellular factors with which they become associated.

Two-hybrid assays may be in accordance with those disclosed by Fields and Song, 1989, Nature 340; 245–246. In such an assay the DNA binding domain (DBD) and the transcriptional activation domain (TAD) of the yeast GAL4 transcription factor are fused to the first and second molecules respectively whose interaction is to be investigated. A functional GAL4 transcription factor is restored only when two molecules of interest interact. Thus, interaction of the molecules may be measured by the use of a reporter gene operably linked to a GAL4 DNA binding site which is capable of activating transcription of said reporter gene. Other transcriptional activator domains may be used in place of the GAL4 TAD, for example the viral VP16 activation domain. In general, fusion proteins comprising DNA binding domains and activation domains may be made.

In the present case polypeptides of the invention may be expressed as fusion proteins with an appropriate domain and candidate second polypeptides with which those of the invention might associate can be produced as fusion proteins with an appropriate corresponding domain. Alternatively libraries such as phage display libraries of such fusion proteins may be screened with a fusion polypeptide of the invention.

B. Antibodies

The provision of the novel polypeptides enables for the first time the production of antibodies able to bind it specifically. Such an antibody may be specific in the sense of being able to distinguish between the polypeptide it is able to bind and other polypeptides of the same species for which it has no or substantially no binding affinity (e.g. a binding affinity of at least about 1000x worse). Specific antibodies bind an epitope on the molecule which is either not present or is not accessible on other molecules. Antibodies according to the present invention may be specific for the wild-type polypeptide. Antibodies according to the invention may be specific for a particular mutant, variant, allele or derivative polypeptide as between that molecule and the wild-type polypeptide, so as to be useful in diagnostic and prognostic methods as discussed below. Antibodies are also useful in purifying the polypeptide or polypeptides to which they bind, e.g. following production by recombinant expression from encoding nucleic acid.

Preferred antibodies according to the invention are isolated, in the sense of being free from contaminants such as antibodies able to bind other polypeptides and/or free of serum components. Monoclonal antibodies are preferred for some purposes, though polyclonal antibodies are within the scope of the present invention.

Antibodies may be obtained using techniques which are standard in the art. Methods of producing antibodies include immunising a mammal (e.g. mouse, rat, rabbit) with a polypeptide of the invention. Antibodies may be obtained from immunised animals using any of a variety of techniques known in the art, and screened, preferably using binding of antibody to antigen of interest. For instance, Western blotting techniques or immunoprecipitation may be used (Armitage et al, Nature, 357:80–82, 1992).

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO092/01047.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Humanized antibodies in which CDRs from a non-human source are grafted onto human framework regions, typically with the alteration of some of the framework amino acid residues, to provide antibodies which are less immunogenic than the parent non-human antibodies, are also included within the present invention.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-0239400. Cloning and expression of chimeric antibodies are described in EP-A-0120694 and EP-A-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The mode of determining binding is not a feature of the present invention and those skilled in the art are able to choose a suitable mode according to their preference and general knowledge.

Antibodies according to the present invention may be used in screening for the presence of a polypeptide, for example in a test sample containing cells or cell lysate as discussed, and may be used in purifying and/or isolating a polypeptide according to the present invention, for instance following production of the polypeptide by expression from encoding nucleic acid therefor. Antibodies may modulate the activity of the polypeptide to which they bind and so, if that polypeptide has a deleterious effect in an individual, may be useful in a therapeutic context (which may include prophylaxis).

An antibody may be provided in a kit, which may include instructions for use of the antibody, e.g. in determining the presence of a particular substance in a test sample. One or more other reagents may be included, such as labelling molecules, buffer solutions, elutants and so on. Reagents may be provided within containers which protect them from the external environment, such as a sealed vial.

C. Nucleic Acid.

The "JMY locus" includes the JMY gene, both the coding sequence (exons) and intervening sequences (introns), and its regulatory elements for controlling transcription and/or translation. We have found, using in situ hybridization, that JMY is located on the long arm of chromosome 5 at 5q13. This region is known to be aberrant in a variety of tumours.

The term "JMY gene" includes normal alleles of the gene which encodes in wild-type mice an mRNA which comprises a sequence substantially corresponding to that of SEQ ID NO. 1. It also includes alleles of this gene carrying one or more variations. The term also includes mammalian species homologues, particularly human homologues.

Our data indicate that the JMY gene product is a transcriptional co-activator protein. Proteins of this type are well-conserved between species and those of skill in the art would recognise that a sequence of this nature from a single species is representative of the genus of eukaryotic, particularly invertebrate and vertebrate, more particularly vertebrate and especially mammalian JMY homologues. In turn, the nucleic acid coding sequences for such JMY proteins will be conserved.

Nucleic acid includes DNA (including both genomic and cDNA) and RNA, and also synthetic nucleic acids, such as those with modified backbone structures intended to improve stability of the nucleic acid in a cell. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or lifespan of polynucleotides of the invention. Where nucleic acid according to the invention includes RNA, reference to the sequences shown in the accompanying listings should be construed as reference to the RNA equivalent, with U substituted for T.

Nucleic acid of the invention may be single or double stranded polynucleotides. Single stranded nucleic acids of the include anti-sense nucleic acids.

The invention further provides ribozymes which comprise a nucleic acid sequence of the invention.

Generally, nucleic acid according to the present invention is provided as an isolate, in isolated and/or purified form, or free or substantially free of material with which it is naturally associated, such as free or substantially free of nucleic acid flanking the gene in the human genome, except possibly one or more regulatory sequence(s) for expression. Nucleic acid may be wholly or partially synthetic and may include genomic DNA, cDNA or RNA.

Nucleic acids of the invention include nucleic acids which comprise a sequence encoding a polypeptide which is selected from the group consisting of residues 1 to 983 of SEQ ID NO. 2 and a polypeptide having at least 70% sequence identity to SEQ ID NO. 2. Preferably the degree of sequence identity in either case is at least 80%, such as at least 90%, 95%, 98% or 99%.

Nucleic acids of the invention further include nucleic acids which comprise a sequence having at least 70% homology, more preferably at least 80%, such as at least 90%, 95%, 98% or 99% sequence homology to the nucleic acid sequences of SEQ ID NO. 1 or its complement.

The invention also provides nucleic acids which are fragments of the nucleic acids described in the two preceding paragraphs. Particular nucleic acids which are preferred include:

(a) nucleic acids which comprise a sequence encoding an active portion of the invention;

(b) nucleic acid fragments of a sequence having at least 70% homology to the nucleic acid sequences of SEQ ID NO. 1 or its complement, said fragments comprising at least 15 nucleotides; and (c) nucleic acids which consist essentially of from 15 to 50, for example from 15 to 35, 18 to 35, 15 to 24, 18 to 30, 18 to 21 or 21 to 24 nucleotides of a sequence having at least 70% homology to the nucleic acid sequence of SEQ ID NO. 1 or its complement.

The nucleic acids (a), (b) and (c) above are not mutually exclusive. Nucleic acids of categories (a) and (b) will include nucleic acids which comprise at least 15, such as at least 20, 30, 50 or 100 nucleotides.

A preferred group of nucleic acid fragments are fragments which consist essentially of from 15 to 50, for example from 15 to 35, 18 to 35, 15 to 24, 18 to 30, 18 to 21 or 21 to 24 nucleotides of SEQ ID NO. 1 or its complement, or variants thereof which contain from 1 to 5, for example 1, 2 or 3 nucleotide substitutions, deletions or insertions, preferably substitutions.

The term "consist essentially of" refers to nucleic acids which do not include any additional 5' or 3' nucleic acid sequences. In a further aspect of the invention, nucleic acids of the invention which consist essentially of from 15 to 30 nucleotides as defined above may however be linked at the 3' but preferably 5' end to short (e.g from 4 to 15, such as from 4 to 10 nucleotides) additional sequences to which they are not naturally linked. Such additional sequences are preferably linkers which comprise a restriction enzyme recognition site to facilitate cloning when the nucleic acid of the invention is used for example as a PCR primer.

Nucleic acids of the invention, particularly short (less than 50) sequences useful as probes and primers may carry a revealing label. Suitable labels include radioisotopes such as $^{32}P$ or $^{35}S$, fluorescent labels, enzyme labels, or other protein labels such as biotin. Such labels may be added to polynucleotides or primers of the invention and may be detected using by techniques known per se.

Also included within the scope of the invention are antisense sequences based on the nucleic acid sequences described herein, preferably in the form of oligonucleotides, particularly stabilized oligonucleotides, or ribozymes. Antisense oligonucleotides may be designed to hybridise to the complementary sequence of nucleic acid, pre-mRNA or mature mRNA, interfering with the production of polypeptide encoded by a given DNA sequence (e.g. either native JMY polypeptide or a mutant form thereof), so that its expression is reduce or prevented altogether. Ribozymes will be designed to cleave mRNA encoded by a JMY nucleic acid sequence of the invention, desirably at a target sequence specific to the JMY sequence.

In addition to the coding sequence, antisense techniques can be used to target the control sequences of the JMY gene, e.g. in the 5' flanking sequence. The construction of antisense sequences and their use is described in Peyman and Ulman, Chemical Reviews, 90:543–584, (1990), Crooke, Ann. Rev. Pharmacol. Toxicol., 32:329–376, (1992), and Zamecnik and Stephenson, P.N.A.S, 75:280–284, (1974). The construction of ribozymes and their use in described in for instance Gibson and Shillitoe, Molecular Biotechnology 7(2): 125–137, (1997).

Antisense and ribozyme sequences of the invention may be introduced into mammalian cells lines in culture to study the function of JMY, for example by causing down-regulation of this gene and observing phenotypic effects, or the expression or location of proteins described herein which associate with JMY. In cells where aberrant expression of JMY occurs, such antisense and ribozyme sequences may be used to down-regulate the expression of the gene.

Nucleic acid sequences encoding all or part of the JMY gene and/or its regulatory elements can be readily prepared by the skilled person using the information and references contained herein and techniques known in the art (for example, see Sambrook, Fritsch and Maniatis, "Molecular Cloning, A Laboratory Manual, Cold Spring Harbor Laboratory Press, 1989, and Ausubel et al, Short Protocols in Molecular Biology, John Wiley and Sons, 1992). These techniques include (i) the use of the polymerase chain reaction (PCR) to amplify samples of such nucleic acid, e.g. from genomic sources, (ii) chemical synthesis, or (iii) preparing cDNA sequences. Modifications to the wild type sequences described herein can be made, e.g. using site directed mutagenesis, to lead to the expression of modified polypeptides or to take account of codon preference in the host cells used to express the nucleic acid.

In general, short sequences for use as primers will be produced by synthetic means, involving a step wise manufacture of the desired nucleic acid sequence one nucleotide at a time. Techniques for accomplishing this using automated techniques are readily available in the art.

Longer polynucleotides (including those from subjects expressing inactive portions) will generally be produced using recombinant means, for example using a PCR (polymerase chain reaction) cloning techniques. This will involve making a pair of primers (e.g. of about 15–50 nucleotides) based on the sequence information provided herein to a region of the mRNA or genomic sequence encoding the mRNA which it is desired to clone, bringing the primers into contact with mRNA or cDNA obtained from a murine or human cell (e.g. a brain cell, particularly a fetal brain cell), performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Such techniques may be used to obtain all or part of the sequences described herein. Genomic clones containing the JMY gene and its introns and promoter regions may also be obtained in an analogous manner, starting with genomic DNA from a murine or human cell, e.g. a primary cell such as a liver cell, a tissue culture cell or a library such as a phage, cosmid, YAC (yeast artificial chromosome), BAC (bacterial artificial chromosome) or PAC (P1/P2 phage artificial chromosome) library.

Polynucleotides which are not 100% homologous to the sequences of the present invention but fall within the scope of the invention can be obtained in a number of ways.

Other murine variants (for example allelic forms) of the JMY gene described herein may be obtained for example by probing cDNA or genomic DNA libraries made from murine tissue.

In addition, other animal, for example fish (such as the Zebra fish), worm (such as *C. elegans*) and particularly mammalian (e.g. rat or rabbit, sheep, goat, pig, or primate particularly human) homologues of the JMY gene may be obtained. Such sequences may be obtained by making or obtaining cDNA libraries made from dividing cells or tissues or genomic DNA libraries from other animal species, and probing such libraries with probes comprising all or part of a nucleic acid of the invention under conditions of medium to high stringency (for example for hybridization on a solid support (filter) overnight incubation at 42° C. in a solution containing 50% formamide, 5×SSC (750 mM NaCl, 75 mM sodium citrate), 50 mM sodium phosphate (pH7.6), 5×Denhardt's solution, 10% dextran sulphate and 20 µg/ml salmon sperm DNA, followed by washing in 0.03M sodium chloride and 0.03M sodium citrate (i.e. 0.2×SSC) at from about 50° C. to about 600° C.).

Thus the present invention provides an isolated nucleic acid which hybridizes to the nucleotide sequence set forth in SEQ ID NO:1 under the abovementioned hybridization and washing conditions. Such a nucleic acid is suitable for use as a probe for detecting the JMY gene, for example in Southern blots or in metaphase spreads.

Alternatively, such polynucleotides may be obtained by site directed mutagenesis of the sequences of SEQ ID NO. 1 or allelic variants thereof. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides. Further changes may be desirable to represent particular coding changes which are required to provide, for example, conservative substitutions.

In the context of cloning, it may be necessary for one or more gene fragments to be ligated to generate a full-length coding sequence. Also, where a full-length encoding nucleic acid molecule has not been obtained, a smaller molecule representing part of the full molecule, may be used to obtain full-length clones. Inserts may be prepared from partial cDNA clones and used to screen cDNA libraries. The full-length clones isolated may be subcloned into expression vectors and activity assayed by transfection into suitable host cells, e.g. with a reporter plasmid.

The present invention also extends to nucleic acid comprising transcriptional control sequences for the JMY gene. Such control sequences will be found 5' to the open reading frame of the JMY gene and are obtainable by probing a genomic DNA library (such as a phage, cosmid, YAC, BAC or PAC library) of a mammal with a nucleic acid of the invention, selecting a clone which hybridizes under conditions of medium to high stringency, and sequencing the clone 5' to the open reading frame of the gene. Where only a small amount of sequence is present in the 5' region, this sequence may be used to reprobe the library to genome walk further upstream. Analysis of the upstream region will reveal control regions for gene expression including control regions common to many genes (i.e TATA and CAAT boxes) and other control regions, usually located from 1 to 10,000, such as 1 to 1000 or 50 to 500 nucleotides upstream of the start of transcription.

To confirm that such regions are the control regions of the gene, they may be linked to a reported gene (such as β-galactosidase) and tested in any suitable in vitro or in vivo system. For example the construct of the control region (e.g. comprising 50 to 500 nucleotides upstream of the start of transcription) and the reporter gene may be used to produce a transgenic animal (see below) and the pattern of expression, both spatially and developmentally, may be compared with that of the JMY gene. Where substantially similar patterns of expression are found, this shows that the construct comprises substantially all of the control region of the wild type gene.

The control region may be mutated to identify specific subregions responsible for transcriptional control. This may be achieved by a number of techniques well known in the art as such, including DNase protection footprint assays, in which the control region is brought into contact with an extract from a cell in which the JMY gene is actively expressed, and the regions of the control region which bind factors in that extract is determined.

Isolated nucleic acid comprising such control regions obtainable by such a method form a further aspect of the present invention.

The present invention further extends to genomic DNA exon sequences found between the introns encoding a JMY gene in an animal subject, such as those mentioned above and including humans. Such exon sequences may be obtained in a manner analogous to that described above for the transcriptional control sequences, with the appropriate genome walking being conducted between the intron sequences. The locations of the exons may be determined by comparing genomic and cDNA sequences of the JMY gene, observing where the sequences line up and diverge, and looking for consensus splice sequences which define intron/exon boundaries.

Exon sequences obtainable by these or analogous methods may be used in the construction of mini-gene sequences which comprise nucleic acid encoding polypeptides of the invention which sequences are interrupted by one or more exon sequences.

Mini-genes may also be constructed using heterologous exons, derived from any eukaryotic source.

Nucleic acid according to the present invention, such as a full-length coding sequence or oligonucleotide probe or primer, may be provided as part of a kit, e.g. in a suitable container such as a vial in which the contents are protected from the external environment. The kit may include instructions for use of the nucleic acid, e.g. in PCR and/or a method for determining the presence of nucleic acid of interest in a test sample. A kit wherein the nucleic acid is intended for use in PCR may include one or more other reagents required for the reaction, such as polymerase, nucleosides, buffer solution etc. The nucleic acid may be labelled. A kit for use in determining the presence or absence of nucleic acid of interest may include one or more articles and/or reagents for performance of the method, such as means for providing the test sample itself, e.g. a swab for removing cells from the buccal cavity or a syringe for removing a blood sample (such components generally being sterile). In a further aspect, the present invention provides an apparatus for screening nucleic acid, the apparatus comprising storage means including the a nucleic acid or the invention or fragment thereof, the stored sequence being used to compare the sequence of the test nucleic acid to determine the presence of mutations.

Polynucleotides or primers of the invention or fragments thereof labelled or unlabelled may be used by a person skilled in the art in nucleic acid-based tests for detecting the JMY gene in the human or animal body. In the case of detecting, this may be qualitative and/or quantitative. Detection includes analytical steps such as those which involve sequencing the gene in full or in part.

Such tests for detecting generally comprise bringing a human or animal body sample containing DNA or RNA into contact with a probe comprising a polynucleotide or primer of the invention under hybridizing conditions and detecting any duplex formed between the probe and nucleic acid in the sample. Such detection may be achieved using techniques such as PCR or by immobilizing the probe on a solid support, removing nucleic acid in the sample which is not hybridized to the probe, and then detecting nucleic acid which has hybridized to the probe. Alternatively, the sample nucleic acid may be immobilized on a solid support, and the amount of probe bound to such a support can be detected. Suitable assay methods of this any other formats can be found in for example WO89/03891 and WO90/13667.

In one embodiment, the sample nucleic acid may be in the form of whole chromosomes, for example as a metaphase spread. The nucleic acid probe or primer of the invention may be labelled with a fluorescent label to detect the chromosomal location of a JMY gene in the spread.

Where a PCR based assay is used in the detection of nucleic acid according to the invention, it is preferred that both primers are nucleic acids according to the present invention. However, one of the two primers may be directed to sequences which flank sequences of the JMY gene or are contained within its exons. Those of skill in the art will be able to select specific pairs of PCR primers using routine skill and knowledge in the light of the present disclosure.

A further method of detection according to the invention is in detecting changes to wild-type JMY genes, including single base changes, using single stranded conformational polymorphism (SSCP) analysis. Nucleic acid sequence from all or part of a JMY DNA or mRNA in a sample is hybridized to a reference sequence, and the mobility of the hybrid is observed in a gel under conditions where any non-hybridized regions within the duplex give rise to changes in mobility.

Nucleic acids of the invention are thus useful in screening a test sample containing nucleic acid for the presence of alleles, mutants and variants, the probes hybridising with a target sequence from a sample obtained from the individual being tested. The conditions of the hybridisation can be controlled to minimise non-specific binding, and preferably stringent to moderately stringent hybridisation conditions are preferred. The skilled person is readily able to design such probes, label them and devise suitable conditions for the hybridisation reactions, assisted by textbooks such as Sambrook et al (1989) and Ausubel et al (1992).

As well as determining the presence of polymorphisms or mutations in the JMY sequence, the probes may also be used to determine whether mRNA encoding the OMY gene is present in a cell or tissue.

Nucleic acid of the invention may be provided in the form of compositions, for example a pharmaceutical composition. Such compositions will include pharmaceutically acceptable carriers and adjuvants. Examples of a suitable carrier include liposomes. Liposomes carrying nucleic acid of the invention (particularly where such nucleic acid is carried by a vector, see below) may be used in methods of gene delivery in gene therapy. Suitable liposome compositions and delivery systems are described in Gill et al, Gene Therapy, Vol.4, No.3, pp.199–209 (1997).

D. Vectors.

Nucleic acid polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

E. Expression Vectors.

Preferably, a polynucleotide of the invention in a vector is operably linked to a control sequence which is capable of providing for the expression of the coding sequence by the host cell, i.e. the vector is an expression vector.

The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage phagemid or baculoviral, cosmids, YACs, BACs, or PACs as appropriate. Vectors include gene therapy vectors, for example vectors based on adenovirus, adeno-associated virus, retrovirus (such as HIV or MLV) or alpha virus vectors.

The vectors may be provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell. The vector may also be adapted to be used in vivo, for example in methods of gene therapy. Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others.

Promoters and other expression regulation signals may be selected to be compatible with the host cell for which the expression vector is designed. For example, yeast promoters include *S. cerevisiae* GAL4 and ADH promoters, *S. pombe* nmt1 and adh promoter. Mammalian promoters include the metallothionein promoter which is can be included in response to heavy metals such as cadmium. Viral promoters such as the SV40 large T antigen promoter or adenovirus promoters may also be used. All these promoters are readily available in the art.

The vectors may include other sequences such as promoters or enhancers to drive the expression of the inserted nucleic acid, nucleic acid sequences so that the polypeptide is produced as a fusion and/or nucleic acid encoding secretion signals so that the polypeptide produced in the host cell is secreted from the cell.

Vectors for production of polypeptides of the invention of for use in gene therapy include vectors which carry a mini-gene sequence of the invention.

For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Vectors may be transformed into a suitable host cell as described above to provide for expression of a polypeptide of the invention. Thus, in a further aspect the invention provides a process for preparing polypeptides according to the invention which comprises cultivating a host cell transformed or transfected with an expression vector as described above under conditions to provide for expression by the vector of a coding sequence encoding the polypeptides, and recovering the expressed polypeptides. Polypeptides may also be expressed in in vitro systems, such as reticulocyte lysate.

A further embodiment of the invention provides host cells transformed or transfected with the vectors for the replication and expression of polynucleotides of the invention. The cells will be chosen to be compatible with the said vector and may for example be bacterial, yeast, insect or mammalian.

Polynucleotides according to the invention may also be inserted into the vectors described above in an antisense orientation in order to provide for the production of antisense RNA or ribozymes.

A still further aspect of the present invention provides a method which includes introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

A further aspect of the present invention provides a host cell containing nucleic acid as disclosed herein. The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell.

Nucleic acids of the invention, particularly when in the form of a recombinant vector, may be used in methods of gene therapy. A construct capable of expressing a nucleic acid of the invention may be introduced into cells of a recipient by any suitable means, such that a polypeptide of the invention, preferably a full length or active portion polypeptide, is expressed in the cells.

The construct may be introduced in the form of naked DNA, which is taken up by some cells of animal subjects, including muscle cells of mammalians. In this aspect of the invention the construct will generally be carried by a pharmaceutically acceptable carrier alone. The construct may also formulated in a liposome particle, as described above.

Such methods of gene therapy further include the use of recombinant viral vectors such as adenoviral or retroviral vectors which comprise a construct capable of expressing a polypeptide of the invention. Such viral vectors may be delivered to the body in the form of packaged viral particles.

Constructs of the invention, however formulated and delivered, will be for use in treating conditions brought about by a defect in the JMY locus, including tumours comprising a translocation at 5q 13. The construct will comprise nucleic acid encoding the polypeptide of the invention linked to a promoter capable of expressing the gene in the target cells. The constructs may be introduced into cells of a human or non-human mammalian recipient either in situ or ex-vivo and reimplanted into the body. Where delivered in situ, this may be by for example injection into target tissue(s) or in the case of liposomes, inhalation.

Gene therapy methods are widely documented in the art and may be adapted for use in the expression of a polypeptide of the invention. See for example WO95/14091 and Walther, Molecular Biotechnology, 6(3): 267–286, (1996) and Blomer, Human Molecular Genetics, Vol.5: 1397–1404, (1996), the disclosures of which are incorporated herein by reference.

F. Assays

This section (section "F") of the present application describes assays of the invention which are based on the interaction between JMY and p300/CBP. For the purposes of brevity, reference is made in this section to JMY or JMY protein or polypeptide, although unless stated to the contrary, this is to be taken to include the above-mentioned active portions and variants of JMY which retain the ability to interact with p300/CBP or to form a homodimer.

Definitions:

"p300/CBP" refers to a family member of the p300/CBP family of co-activators which have histone acetyltransferase activity. p300 is described for example by Eckner et al, 1994 and CBP by Bannister and Kouzarides, 1996. For the purposes of the present invention, reference to p300/CBP refers to human allelic and synthetic variants of p300, and to other mammalian variants and allelic and synthetic variants thereof, as well as fragments of said human and mammalian forms of p300. Synthetic variants include those which have at least 80%, preferably at least 90%, homology to p300.

More preferably such variants correspond to the sequence of p300 but have one or more, e.g. from 1 to 10, such as from 1 to 5, substitutions, deletions or insertions of amino acids.

Fragments of p300 and its variants are preferably at least 20, more preferably at least 50 and most preferably at least 200 amino acids in size. The p300/CBP molecule will however retain the ability to physically associate in vivo with JMY.

Preferably, the p300/CBP used in assays of the present invention will also retain the ability to interact with the tumour suppressor molecule p53, as described in the accompanying examples and by Lill et al, 1997.

For the purposes of the present invention, the precise form and structure of a p300/CBP protein or fragment thereof may be varied by those of skill in the art, having regard to the particular assay format to be used.

"p53" refers to the tumour suppressor gene or its encoded amino acid sequence of as reported, for example, by Matlashewski et al (EMBO J. 13; 3257–62, 1984) or Lamb and Crawford (Mol. Cell. Biol. 5; 1379–85, 1986). These sequences are available on Genbank. Wild-type human p53 protein includes a proline/arginine polymorphism at amino acid 72, reflecting a corresponding polymorphism in the gene.

"A p53 molecule" includes wild type p53 from humans and other mammals, particularly primates and rodents including mice and rats. It further includes mutated forms of p53 as found in many tumour cells. Such mutations include point mutations, for example from 1 to 10, e.g from 1 to 5 point mutations (which point mutations result in a change to the amino acid sequence) to the wild-type sequences. It further includes fragments of wild-type and mutated p53 which retain the ability to physically associate in vivo with p300/CBP. Such fragments are preferably at least 20, more preferably at least 30 and most preferably at least 50 amino acids in size.

The estrogen receptor is a 66 kd protein which functions as hormone-activated transcription factor. A number of mammalian sources of the ER are available, including the human ER. Receptor activation is thought to be a consequence of ligand-induced conformational changes in the structure of the receptor. The complex of estrogen with its receptor binds with a high affinity to a well-defined 13-bp palindromic sequence, the estrogen response element (ERE). The ERE is usually located upstream of an estrogen-responsive gene. Estrogen responsive genes include progesterone receptor and PS-2. Transcriptional activation of these genes is involved in estrogen-responsive tumour growth. Reference to the "estrogen receptor" or "ER" includes mammalian ERs as well as fragments and mutants of the estrogen receptor which retain the ability to function as a co-activator with JMY may also be used, and such fragments and mutants may be obtained by methods analogous to those described above for other proteins. Suitable fragments may be determined by routine experimentation. Fragments may be, for example, from 100 to 500 amino acids in length. Reference herein to the estrogen receptor includes fragments and mutants which retain the ability to interact with JMY.

An "E2F family member" includes component members of the heterodimeric transcription E2F transcription factor. These component members include the E2F-1, -2, -3, -4 and -5 family members and the DP protein family members, particularly DP-1 and the various isoforms of DP-3, such as DP-3α. E2F component members are described widely throughout the literature. Reference may be made to Helin et al, Cell 70, 337–350 (1992) or Kaelin et al, Cell 70, 351–364 (1992) for E2F-1, Ivey-Hoyle et al, Mol. Cell. Biol. 13, 7802–7812 (1993) for E2F-2, Lees et al, Mol. Cell. Biol. 13, 7813–7825 (1993) for E2F-3, Beijersbergen et al, Genes and Dev., 8, 2680–2690 (1994) and WO96/15243 for E2F-4, and Hijmans et al, Mol. Cell. Biol. 15, 3082–3089 (1995) and WO96/25494 for E2F-5, all of which are incorporated herein by reference. For DP-1, see WO94/10307 and for DP-3 and its isoforms see WO9743647, which are incorporated herein by reference.- We have found that E2F family members, particularly E2F-x (where x is 1, 2, 3, 4 or 5) family members are also coactivated by JMY. Particularly preferred is E2F-1. E2F family members from any suitable mammalian source may be used, or fragments or variants thereof which retain the ability to be activated by JMY, which activation may be determined using methods such as those illustrated in the accompanying examples.

Assays according to the invention may be performed in vitro in any format available to the person skilled in the art. The precise format of the assay of the invention may be varied by those of skill in the art using routine skill and knowledge.

For example, the interaction between JMY (as defined at the start of this section) and p300/CBP may be studied by labelling one with a detectable label and bringing it into contact with the other which has been immobilised on a solid support. Suitable detectable labels include $^{35}$S-methionine which may be incorporated into recombinantly produced JMY and/or p300/CBP. The recombinantly produced JMY and/or p300/CBP may also be expressed as a fusion protein containing an epitope which can be labelled with an antibody.

The protein which is immobilized on a solid support may be immobilized using an antibody against that protein bound to a solid support or via other technologies which are known per se. A preferred in vitro interaction may utilise a fusion protein including glutathione-S-transferase (GST). This may be immobilized on glutathione agarose beads. In an in vitro assay format of the type described above the putative modulator compound can be assayed by determining its ability to modulate the amount of labelled JMY or p300/CBP which binds to the immobilized GST-p300/CBP or GST-JMY, as the case may be. This may be determined by fractionating the glutathione-agarose beads by SDS-polyacrylamide gel electrophoresis. Alternatively, the beads may be rinsed to remove unbound protein and the amount of protein which has bound can be determined by counting the amount of label present in, for example, a suitable scintillation counter.

Alternatively an antibody attached to a solid support and directed against one of JMY or p300/CBP may be used in place of GST to attach the molecule to the solid support. Antibodies against JMY and p300/CBP may be obtained in a variety of ways known as such in the art, and as discussed herein.

In an alternative mode, one of JMY and p300/CBP may be labelled with a fluorescent donor moiety and the other labelled with an acceptor which is capable of reducing the emission from the donor. This allows an assay according to the invention to be conducted by fluorescence resonance energy transfer (FRET). In this mode, the fluorescence signal of the donor will be altered when JMY and p300/CBP interact. The presence to a candidate modulator compound which modulates the interaction will increase the amount of unaltered fluorescence signal of the donor.

FRET is a technique known per se in the art and thus the precise donor and acceptor molecules and the means by which they are linked to JMY and p300/CBP may be accomplished by reference to the literature.

Suitable fluorescent donor moieties are those capable of transferring fluorogenic energy to another fluorogenic molecule or part of a compound and include, but are not limited to, coumarins and related dyes such as fluoresceins, rhodols and rhodamines, resorufins, cyanine dyes, bimanes, acridines, isoindoles, dansyl dyes, aminophthalic hydrazines such as luminol and isoluminol derivativess aminophthalimides, aminonaphthalimides, aminobenzofurans, aminoquinolines, dicyanohydroquinones, and europium and terbium complexes and related compounds.

Suitable acceptors include, but are not limited to, coumarins and related fluorophores, xanthenes such as fluoresceins, rhodols and rhodamines, resorufins, cyanines, difluoroboradiazaindacenes, and phthalocyanines.

A preferred donor is fluorescein and preferred acceptors include rhodamine and carbocyanine. The isothiocyanate derivatives of these fluorescein and rhodamine, available from Aldrich Chemical Company Ltd, Gillingham, Dorset, UK, may be used to label JMY and p300/CBP. For attachment of carbocyanine, see for example Guo et al, J. Biol. Chem., 270; 27562–8, 1995.

The above assay formats may also be used to determine the ability of a putative modulator compound to modulate the interaction of JMY with an ER, or JMY with an E2F family member, particularly and E2F-x family member such as E2F-1. Such assays are optionally performed in the presence of a p300/CBP polypeptide.

Assays of the invention may also be performed in vivo. Such an assay may be performed in any suitable host cell, e.g a bacterial, yeast, insect or mammalian host cell. Yeast and mammalian host cells are particularly suitable.

To perform such an assay in vivo, constructs capable of expressing JMY and p300/CBP and a reporter gene construct may be introduced into the cells. This may be accomplished by any suitable technique, for example calcium phosphate precipitation or electroporation. The three constructs may be expressed transiently or as stable episomes, or integrated into the genome of the host cell.

In vivo assays may also take the form of two-hybrid assays wherein JMY and p300/CBP are expressed as fusion proteins, one being a fusion protein comprising a DNA binding domain (DBD), such as the yeast GAL4 binding domain, and the other being a fusion protein comprising an activation domain, such as that from GAL4 or VP16. In such a case the host cell (which again may be bacterial, yeast, insect or mammalian, particularly yeast or mammalian) will carry a reporter gene construct with a promoter comprising a DNA binding elements compatible with the DBD. The reporter gene may be a reporter gene as disclosed above. The promoters for the genes may be those discussed above.

JMY and p300/CBP and the reporter gene, may be introduced into the cell and expressed transiently or stably.

Since we have also found that the JMY gene product has a homodimerization interface, through which heterodimers of JMY can form, the assay formats described above are also suitable for assaying for modulators of JMY homodimerization. These assays may be conducted as described above, by providing a second JMY polypeptide in place of the p300/CBP.

Alternatively, assays of the invention may be conducted by utilizing the ability of a JMY-p300/CBP complex to mediate the activation of a reporter gene or to induce a cellular response in a cell, particularly apoptosis. For example, a number of transcription factors, including the glucocorticoid receptor (GR) and E2F-1, are known to be regulated by p300/CBP, as is p53. We have found that the regulation of such factors is enhanced by JMY. We have also found that JMY is a coactivator of ER. Further, we have found that p53-mediated apoptosis is enhanced by the presence of JMY and p300. The JMY in such a complex may be in the form of a homodimer.

Thus assays of the invention include an assay for a modulator of JMY-p300/CBP complex formation which comprises:

a) providing JMY and p300/CBP together with a regulatory factor which is a target for p300/CBP, in the presence of a putative modulator and a reporter gene which comprises a target promoter for said regulatory factor; and b) measuring the modulation of transcription of the reporter gene caused by the presence of said modulator.

The regulatory factor includes GR for which suitable promoters include promoters which contain a GRE such as c-myc and the MMLV LTR; E2F-1 for which suitable promoters include cyclin A, cyclin E, tyrosine amino transferase and the E2F-1 gene promoter; p53 for which suitable promoters include Bax, Wafl/Cip, Gadd45 and cyclin G; ER for which suitable promoters include progesterone receptor and PS-2; and other nuclear receptors and promoters containing recognition elements of this type. Suitable reporter genes operably linked to the promoter include chloramphenicol acetyl transferase, luciferase, green fluorescent protein and β-galactosidase. In the case of ER, a the 13 base palindromic estrogen response element (ERE) may be included in the promoter of a reporter construct to provide a suitable reporter gene.

In an alternative embodiment, the assay may be conducted in a cell lacking wild-type p53 and which undergoes apoptosis in the presence of p53. Such cells include SAOS-2 cells. In this format the assay will be conducted by supplying to the cell expression vector(s) encoding JMY, p300/CBP and wild type p53, treating said cells with a putative modulator and measuring the effect of the modulator on apoptosis of the cells. Apoptosis may also be measured in an analogous manner in cell lines with wild type p53 wherein apoptosis is enhanced by the presence of, for example, excess JMY.

In another alternative embodiment, the interaction of ER with JMY may be measured as described above in the absence of a p300/CBP protein. We have found that, particularly in the presence of an estrogen, such as 17beta estradiol, the two proteins interact in a cell. A convenient assay format is to provide the ER in the form of a fusion protein comprising a DNA binding domain, such as the gal4 DNA binding domain. This may be used to determine the activation of a reporter construct comprising a promoter which is bound by the DNA binding domain. We have found that JMY acts as a transactivator to provide for expression of the reporter gene of the reporter construct.

Assays will be run with suitable controls routine to those of skill in the art.

Additional Assay Components.

The interaction between JMY and p300 which we have established may be influenced in the cell by the actions of, inter alia, E2F-1 and pRb. It may thus be desirable to include an E2F-1, and E2F-x or other E2F family member and/or a pRb molecule in the assay of the invention. Such molecules may be included in both in vitro and in vivo assays. They may also be obtained by recombinant production, and expressed where appropriate using constructs and means analogous to those described above for the JMY and p300 molecules.

Cell Lines.

The assays of the invention give rise to novel cell lines useful in performing the assays. Such cell lines form a further aspect of the invention.

In a preferred aspect, cell lines of the invention will comprise:
(a) a first nucleic acid construct comprising nucleic acid encoding a JMY polypeptide operably linked to a promoter; and
(b) a second nucleic acid construct comprising nucleic acid encoding a p300/CBP polypeptide operably linked to a promoter,
wherein at least one of said promoters, preferably both, is heterologous to the nucleic acid to which it is operably linked.

The cell line may further comprise:
(c) a nucleic acid construct comprising a p53 binding operably linked to a promoter and a sequence encoding a detectable gene product; and
(d) a nucleic acid construct encoding and capable of expressing a p53 molecule capable of binding to a p53 binding site.

In another aspect, cell lines of the invention will comprise:
(a) a first nucleic acid construct comprising nucleic acid encoding a JMY polypeptide operably linked to a promoter; and
(b) a second nucleic acid construct comprising nucleic acid encoding an ER polypeptide operably linked to a promoter,
wherein at least one of said promoters, preferably both, is heterologous to the nucleic acid to which it is operably linked.

Preferably one of (a) and (b) is in the form of a fusion protein comprising a DNA binding domain.

The nucleic acid constructs may be DNA or RNA. They may be carried stably in the genome of the cell or in the form of non-integrated plasmid vectors.

Host cell lines include in particular yeast and mammalian, especially human, cell lines, including those mentioned elsewhere herein.

A putative modulator compound may be one which enhances, stabilizes or inhibits the various interactions described above, and thus reference to "modulation" includes both enhancement, stabilization or inhibition of said interactions.

G. Transgenic Animals

In another aspect of the invention, there is provided a method for producing a transgenic non-human mammal, particularly a rodent such as a mouse, by incorporating a lesion into the locus of a JMY gene.

This may be achieved in a variety of ways. A typical strategy is to use targeted homologous recombination to replace, modify or delete the wild-type JMY gene in an embryonic stem (ES) cell. An targeting vector is introduced into ES cells by electroporation, lipofection or microinjection. In a few ES cells, the targeting vector pairs with the cognate chromosomal DNA sequence and transfers the desired mutation carried by the vector into the genome by homologous recombination. Screening or enrichment procedures are used to identify the transfected cells, and a transfected cell is cloned and maintained as a pure population. Next, the altered ES cells are injected into the blastocyst of a preimplantation mouse embryo or alternatively an aggregation chimera is prepared in which the ES cells are placed between two blastocysts which, with the ES cells, merge to form a single chimeric blastocyst. The chimeric blastocyst is surgically transferred into the uterus of a foster mother where the development is allowed to progress to term. The resulting animal will be a chimera of normal and donor cells. Typically the donor cells will be from an animal with a clearly distinguishable phenotype such as skin colour, so that the chimeric progeny is easily identified. The progeny is then bred and its descendants cross-bred, giving rise to heterozygotes and homozygotes for the targeted mutation. The production of transgenic animals is described further by Capecchi, M, R., 1989, Science 244; 1288–1292; Valancius and Smithies, 1991, Mol. Cell. Biol. 11; 1402–1408; and Hasty et al, 1991, Nature 350; 243–246, the disclosures of which are incorporated herein by reference.

Homologous recombination in gene targeting may be used to replace the wild-type JMY gene with a specifically defined mutant form (e.g truncated or containing one or more substitutions).

The invention may also be used to replace the wild-type gene with a modified gene capable of expressing a wild-type or otherwise active JMY polypeptide, where the expression may be selectively blocked either permanently or temporarily. Permanent blocking may be achieved by supplying means to delete the gene in response to a signal. An example of such a means is the cre-lox system where phage lox sites are provided at either end of the transgene, or at least between a sufficient portion thereof (e.g. in two exons located either side or one or more introns). Expression of a cre recombinase causes excision and circularisation of the nuclei acid between the two lox sites. Various lines of transgenic animals, particularly mice, are currently available in the art which express cre recombinase in a developmentally or tissue restricted manner, see for example Tsien, Cell, Vol.87(7): 1317–1326, (1996) and Betz, Current Biology, Vol.6(10): 1307–1316 (1996). These animals may be crossed with lox transgenic animals of the invention to examine the function of the JMY gene. An alternative mechanism of control is to supply a promoter from a tetracyline resistance gene, tet, to the control regions of the JMY locus such that addition of tetracyline to a cell binds to the promoter and blocks expression of the JMY gene.

Transgenic targeting techniques may also be used to delete the JMY gene. Methods of targeted gene deletion are described by Brenner et al, WO94/21787 (Cell Genesys), the disclosure of which is incorporated herein by reference.

Homologous recombination may also be used to produce "knock in" animals which express a polypeptide of the invention in the form of a fusion protein, fused to a detectable tag such as β-galactosidase or green fluorescent protein. Such transgenic non-human mammals may be used in methods of determining temporal and spatial expression of the JMY gene by monitoring the expression of the detectable tag.

A further alternative is to target control sequences responsible for expression of the JMY gene.

The invention extends to transgenic non-human mammals obtainable by such methods and to their progeny. Such mammals may be homozygous or heterozygous. Such mammals include mice, rodents, rabbits, sheep, goats, pigs.

Transgenic non-human mammals may be used for experimental purposes in studying the role of JMY in regulating the cell cycle and in the development of therapies designed to target the interaction of JMY with other cellular factors, particularly p300/CBP, ER or and E2F family member. By "experimental" it is meant permissible for use in animal experimentation or testing purposes under prevailing legislation applicable to the research facility where such experimentation occurs.

EXAMPLE 1

Characterization of JMY.

(a) The nucleic acid sequence (SEQ ID NO: 1) and primary amino acid sequence of JMY was determined (983 amino acid residues (SEQ ID NO:2). The central p300 binding domain in JMY is from residue 469 to 558. This contains hydrophobic residues that conform to a heptad leucine-rich repeat. The adenovirus E1a CR2-like motif, EVQFEILKCE (SEQ ID NO:3), is at residues 530 to 540 (residues in bold being conserved in E1a CR2). There is a proline-rich C-terminal region at residues 794–818.

(b) Expression of JMY was determined by Northern blot analysis of RNA prepared from mouse tissues. Expression of a 9.5kb transcript was observed in heart, brain, spleen, lung, skeletal muscle, kidney and testis although the levels differ from tissue to tissue. A minor transcript at 6kb is apparent in liver and the abovementioned tissues apart from testis which express abundant 4.5Kb transcript. As a control, β-actin RNA was used.

example 2

JMY interacts with p300.

(a) Yeast two-hybrid assays were performed using the baits pLex-p300$^{611-2283}$ or pLex-JMY$^{469-558}$ with pVP16-JMY$^{469-558}$ and pGAD-E1a. The results are shown in Table 1. Induction of β-galactosidase (+in Table 1) indicated the major p300 interacting domain was in the central 469 to 558 segment of JMY.

TABLE 1

| ↓Bait\Prey→ | VP16 | GAD-E1a | VP16-JMY$^{469-558}$ |
|---|---|---|---|
| LexA | − | − | − |
| LexA-p300$^{611-2283}$ | − | + | + |
| Lex-JMY$^{469-558}$ | − | − | + |

(b) Co-immunoprecipitation of JMY and p300 from U2OS cells transfected with pG4 (30 μg) was performed as described. After extraction, immunoprecipitation was performed with anti-Ga14 followed by immunoblotting with anti-HA (12CA5). As a control, the cell extract was immunoblotted with an anti-peptide JMY antibody in the absence or presence of competing homologous peptide. The results, which are discussed in detail below, confirmed that JMY interacts with p300 in vivo.

(c) The mammalian two-hybrid assay was performed in U2OS cells transfected with the indicated expression vectors, namely pVP16-JMY$^{469-558}$ (5 μg) together with pG4 or pG4-p300$^{611-2283}$ (1 μg). The findings (illustrated schematically in FIG. 1) corroborate those of (b) above.

EXAMPLE 3

JMY interacts with two domains in p300

(a) Two-hybrid assay in mammalian cells were performed pG4-p300 expression vectors (1 μg) were introduced into U2OS cells either alone or together with pVP16-JMY$^{469-558}$ (5 μg) and the reporter pG5-luc. The relative activity of luciferase to β-galactosidase (derived from the internal control pCMV-βgal) was determined as the average of two treatments (FIG. 2). The activity of both pG4-p300$^{611-1257}$ and pG4-p300$^{1572-2283}$ underwent a 4- and 5-fold increase in the presence of pVP16-JMY$^{469-558}$.

(b) Binding of p300 to JMY was determined. Three different GST-p300 fusion proteins were incubated with either in vitro translated 13S E1a or JMY$^{335-588}$. The three proteins were A: GST-p300$^{1-596}$; B: GST-p300$^{744-1571}$; and C: GST-p300$^{1572-237}$. The amount of each protein bound was assessed as described below. The interaction between the 13S E1a polypeptide and GST-p300$^{1572-2370}$ served as a positive control, and both GST-p300$^{744-1571}$ and GST-p300$^{1572-2370}$ were found to bind JMY. About 10% of the input JMY bound to each p300 fusion protein.

EXAMPLE 4

JMY co-activates p53 and augments apoptosis.

(a) The p53 reporter pBax-luc (2 μg) together with h expression vectors for wild-type p53 (0.25 μg), JMY (4 or 8 μg) either alone or together with p300 (0.2 μg) were transfected into SAOS2 (p53$^{-/-}$) cells. Average of duplicate readings of the relative level of luciferase to the β-galactosidase activity from the internal control were taken (FIG. 3).

(b) Expression vectors for p53 either alone or together with JMY were introduced into SAOS2 cells as described in the methods. Cells were fixed and treated with the anti-p53 monoclonal antibody 421 or assayed for the level of apoptosis by TUNEL. The results showed co-expression of JMY with p53 enhanced apoptosis.

(c) A quantitative comparison of the effect on apoptosis in SAOS2 cells caused by JMY, p300 or both in the presence or absence of p53 was made. The percentage of p53-positive (determined by monoclonal antibody 421) cells that were TUNEL-positive was derived, and compared to values obtained in the presence of JMY, p300, or both. The percentage increase in apoptosing cells was determined. The level of apoptosing cells caused by p53 was 17.7%, and when co-expressed with JMY apoptosis increased to 23.1%, with p300 to 16.94% and when p53 was co-expressed with JMY and p300 the level of apoptosis increased to 30.17%. The TUNEL-positive population was compared to the number of DAPI-positive cells in the absence of p53. This was used to assess the level of apoptosis in the presence of JMY and p300 which was 2.25% and 2.88% respectively. The values given were obtained from two separate assays.

EXAMPLE 5

JMY possesses the properties of a co-activator and co-operates with p300 in the transcriptional activation of the glucocorticoid receptor and E2F-1.

(a) The GR reporter pGRE-cat (1 μg) together with expression vectors for JMY (1, 3 or 5 μg) either alone or together with p300 (3 μg) were transfected into HeLa cells in the absence or presence of the ligand dexamethasone (0.5 μM) for the glucocorticoid receptor. The average of triplicate readings were taken to determine the relative level of CAT activity to total protein. There was significantly greater activity when both JMY and p300 were expressed together (FIG. 4a)

Figure 4B:
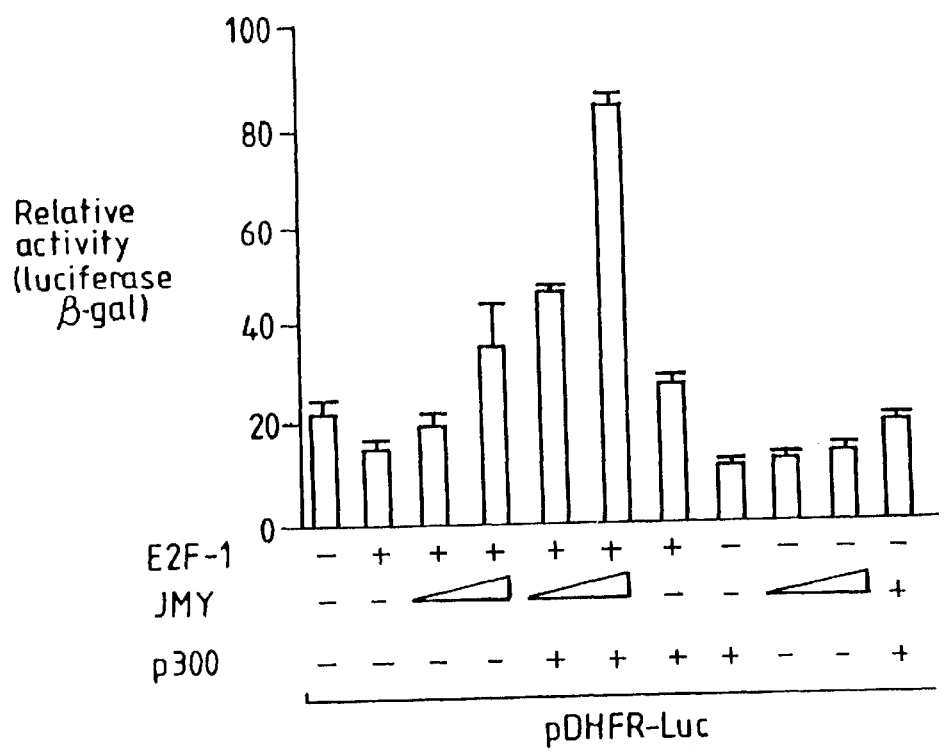
FIG. 4B shows that co-expression of JMY and p300 induce transcriptional activity of E2F-1.

(b) The E2F reporter pDHFR-luc (1 µg) together with expression vectors for E2F-1 (0.2 µg) either alone or together with p300 (3 µg) and JMY (4 and 8 µg) were transfected into SAOS2 cells. The average of duplicate readings relating to the level of luciferase to β-galactosidase were taken. The results showed co-expression of either JMY and p300 induce the transcriptional activity of E2F-1, and the effect is greater when both are co-expressed (FIG. 4b).

EXAMPLE 6.

JOM is a potent coactivator of the estrogen receptor.

The estrogen receptor is another transcription factor known to respond to p300/CBP (Hanstein et al 1996, ref 38). In order to determine whether JMY can stimulate transcription mediated by the estrogen receptor, transient transfection assays were carried out in which a reporter gene under the control of the estrogen receptor was co-transfected into U2-OS cells (a transformed osteoblast cell line, see ATCC catalogue) together with a construct encoding the JMY co-activator protein.

Transient transfection assays.

U2-OS cells were maintained in DMEM supplemented with 10% foetal bovine serum. Twenty-four hours before transfection, cells were maintained in DMEM without phenol red containing 5% charcoal stripped FBS. Transfections were performed in duplicate in 60 mm plates using calcium phosphate; each transfection included 10 µg G5B-luciferase expression vector, 1 µg β-galactosidase expression vector (internal control) and 1 µg gal4-estrogen receptor and/or CMV-coactivator expression plasmids as indicated. After 16 hours, the cells were glycerol shocked, washed with PBS and incubated in fresh medium supplemented with 10nM estradiol or vehicle. After a further 30 hours, the cells were harvested and assayed for luciferase and β-galactosidase activities. The β-galactosidase activity was used to correct for differences in transfection efficiency.

Constructs.

pG5-luciferase is as described above.

pCMVcyclin D1 and pCMVSRC1 consist of the full length sequences of Cyclin D1 (Xiong et al 1991, ref 36) and SRC1 (Onate et al 1995, ref 33) in pCMV (pRcCMV from Invitrogen Inc).

gal4-ER is the full length estrogen receptor sequence (Greene et al, ref 37) linked to the DNA binding domain of gal4 (as described above).

RESULTS

Figure 5:
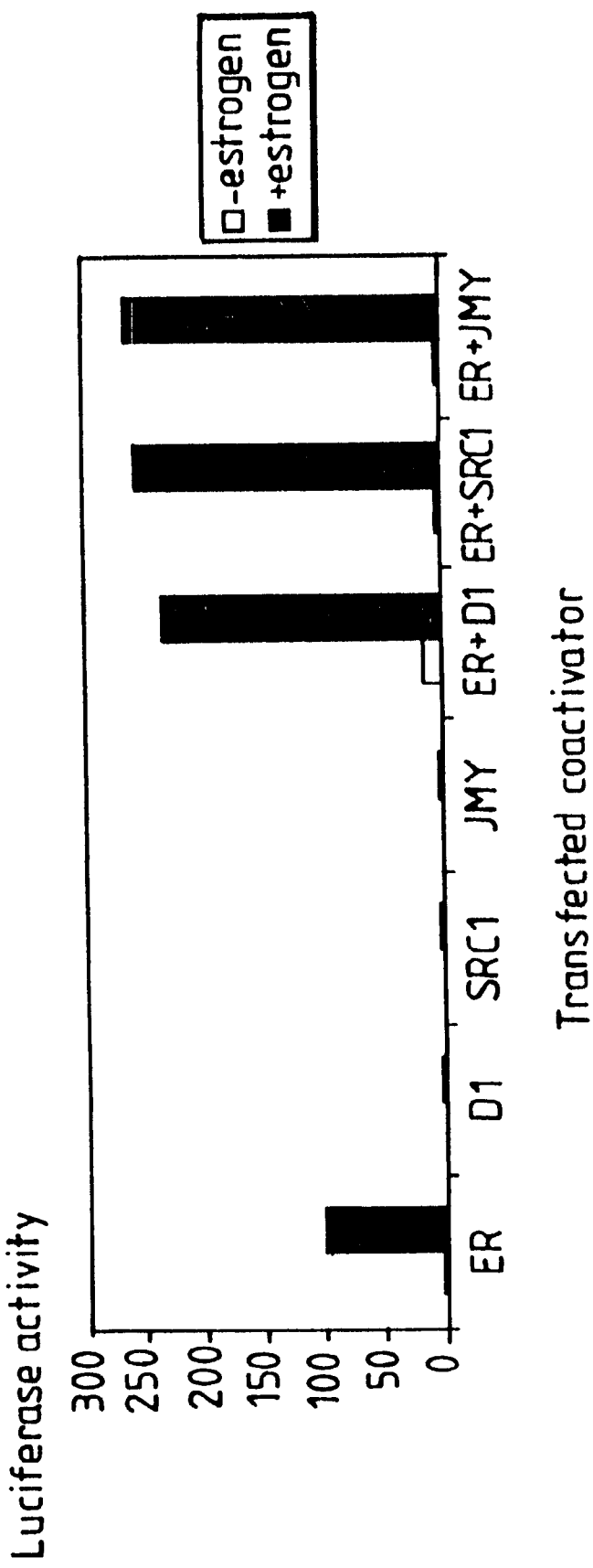
FIG. 5 shows that JMY is a co-activator of the estrogen receptor (ER).

This results are shown in FIG. 5. It can be seen that although JMY does not by itself activate estrogen receptor mediated transcription, it acts as a potent coactivator in the presence of estrogen. It is as potent as the known coactivators cyclin D1 (Neuman et al, ref 34; Zwijsen et al, ref 35), and SRC1 (Onate et al, ref 33). The estrogen receptor is therefore another transcription factor responding to p300/CBP for which JMY acts as a potent coactivator.

EXAMPLE 7

JMY interacts directly with E2F-1 and TBP

GST-pull down assays were performed to assess the interaction of JMY and portions thereof with E2F-1 and TATA-box-binding protein TBP (Sadovsky et al., 1995, ref 39). The interaction between E2F-1 and JMY 1-117 (amino acid residue numbering), JMY 1-504, JMY 541-868 and JMY 1-983 was studied. E2F-1 and TBP proteins were expressed and labelled in an in vitro in a reticulocyte cell lysate, and the lysate mixed with 2 µg of JMY protein portions which were expressed as GST fusion proteins and recovered from a bacterial host expression system.

The data show that E2F-1 binds directly to JMY in the C-terminal portion (541–868), whereas binding to TBP is predominantly in the N-terminal portion (1–504, and less strongly, 1–117). This shows JMY comprises at least two domains which interact directly with transcription factors and provide for transactivation of these factors.

DISCUSSION

To elucidate the mechanisms of transcriptional activation by p300/CBP, we considered the possibility that additional control may be exerted through proteins that physically interact with and regulate the activity of p300/CBP. This possibility was investigated by screening for p300-interacting proteins by the yeast two-hybrid approach using a truncated p300, namely $p300^{611-2283}$, fused to the LexA DNA binding domain. Although pLexA-$p300^{611-2283}$ failed to activate transcription, it retained the ability to interact with a known p300/CBP-binding protein, the adenovirus E1a protein (ref.4). Using pLexA-$p300^{611-2283}$ as the bait we screened a 10.5 d.p.c mouse embryo activation domain-tagged library and identified a new protein, which we have called JMY (for junction-mediating and regulatory protein).

The JMY polypeptide has a predicted molecular weight of 110kD and lacks significant similarity to any other known protein. The protein sequence of JMY possesses a number of interesting features, such as a central region with a heptad hydrophobic residue (mostly leucine) repeat, together with a motif that resembles conserved region (CR) 2 in the adenovirus E1a protein, and a C-terminal domain rich in proline residues. The major species of RNA that encodes JMY is about 9kb with a less abundant transcript at 6kb; both transcripts are expressed in a wide variety of mouse tissues, apart from testis, where a smaller transcript exists.

To identify the region in JMY that is necessary for the interaction with p300/CBP, we assayed the activity of JMY derivatives as LexA hybrids in the yeast two-hybrid assay. The major p300 interacting domain in JMY was located in a 90 residue central segment, between amino acid residue 469 and 558. This same region, which contains hydrophobic residues in a heptad repeat, when assayed in the yeast two-hybrid assay can also act as a functional dimerization interface.

To determine whether p300 and JMY can interact in mammalian cells we used both immunochemical and two-hybrid based approaches. Co-transfection of U2OS cells with expression vectors encoding p300 and JMY, followed by immunoprecipitation and immunoblotting, confirmed that the interaction occurs in mammalian cells since the 110kD JMY polypeptide was present in the p300 immuno-precipitation but not the control treatment. These findings were corroborated in the mammalian two-hybrid assay in which p300 as a fusion protein with the Gal4 DNA binding domain, G4-$p300^{611-2283}$, efficiently interacted with a hybrid protein containing the central domain of JMY (residues 469 to 558) fused to the VP16 transcriptional activation domain in VP16-$JMY^{469-558}$ Thus, JMY and p300/CBP proteins can interact in mammalian cells.

The region in p300 that is responsible for the interaction with JMY was determine during a mammalian two-hybrid assay and a panel of p300 deletion mutants fused to the Gal4 DNA binding domain. The interaction between JMY and p300 occurred with two regions in p300, one in the C-terminal region, encompassed within residues 1572 to 2283, and the other within 611 to 1257, because when JMY-VP16 was co-expressed with either G4-p300$^{1572-2283}$ or G4-p300$^{611-1257}$ the transcriptional activity of the reporter pG5-luc was far more efficient than that observed in the presence of the bait alone. Other regions of p300, such as from residue 1302 to 1572, failed to interact with JMY-VP16.

Furthermore, an interaction between JMY and p300 was evident by taking a biochemical approach in which different regions of p300 expressed as GST-fusion proteins were incubated with in vitro translated JMY. As expected, an interaction between adenovirus E1a and the C-terminal region of p300 was evident. In support of the two-hybrid assay, two regions within GST-p300$^{744-1571}$ and GST-p300$^{1572-237}$, bound to JMY, these same two regions overlapping with the Ga14-p300 hybrid proteins assayed earlier. These biochemical data support the conclusion that JMY interacts with two regions in p300. Thus, JMY interacts with two regions in p300, one of which resides in the C-terminal region of p300 and is known to be recognised by other regulatory proteins, including adenovirus E1a, the tumour suppressor protein p53[7,8,9] and P/CAF[1].

Next, we examined the possibility that JMY possessed the properties of a transcriptional regulator, firstly, by studying the effect of JMY on p53, a transcription factor which is known to be a target for p300/CBP proteins [7,8,9]. The transcriptional activity of p53 was assayed on the promoter taken from the Bax gene, which responds to p53 and encodes a protein that facilitates apoptosis[19]. The Bax promoter was efficiently induced in the presence of exogenous p53 in SAOS2 cells, cells in which the endogenous p53 gene is inactivated. A titratable increase in p53-dependent transcription was also apparent in the presence of JMY, but a further enhancement occurred when p300 was co-expressed. Similar results were observed in cell-types other than SAOS2, with the effect dependent upon the integrity of the N-terminal activations domain in p53. The transcription of other p53 target genes, such as Waf1/Cip1,[22] also was enhanced by co-expression of JMY although to a lesser extent than the Bax promoter. These data indicate that JMY possesses the properties of a co-activator and, furthermore, acts together with p300/CBP proteins in the transcriptional activation of p53.

To explore the biological consequence of co-activation by JMY, we evaluated the effect of JMY on wild-type p53 activity which, when induced by genotoxic stress can, in some circumstances, cause apoptosis[18,19,20,21]. For This analysis we used SAOS2 cells, which are sensitive to p53-dependent apoptosis upon the introduction of wild-type p53[23]. Although apoptosis was evident with p53 alone, the co-expression of JMY with p53 significantly enhanced the level of apoptosis, resulting in an increase of about 30% in the total number of cells undergoing apoptosis. This influence of JMY on apoptosis was not apparent in the absence of p53, indicating that the process is dependent upon the presence of wild-type p53. In contrast however, p300 failed to affect the apoptotic activity of p53, despite causing an increase in p53-dependent transcription, although the level of p53-dependent apoptosis was significantly greater when JMY and p300 were co-expressed. These date indicate that, the induction of p53-dependent apoptosis caused by JMY can be further enhanced by p300 and, further, that an increased level of p300 alone is not sufficient to promote apoptosis.

We assessed the generality of the co-activator properties of JMY by studying the effects on two other p300/CBP-regulated transcription factors, namely the glucocorticoid receptor (GR)[24] and E2F-1[9]. In HeLa cells, where the endogenous GR functions in a ligand-dependent fashion, the co-expression of JMY or p300 potentiated the transcriptional activity of a GR-responsive promoter. As observed with p53, there was significantly greater activity when both JMY and p300 were expressed together. Thereafter, the effect of JMY on E2F-1 was explored by studying the E2F-responsive promoter taken from the DHFR gene[25]. The co-expression of either JMY or p300 induced the transcriptional activity of E2F-1 and, again, the effect was much greater when both JMY and p300 were introduced together compared to either alone. We conclude that JMY possessed the properties of a co-activator and, furthermore, enhances the transcriptional activity of transcription factors that respond to p300/CBP proteins.

The p300/CBP proteins are pleiotrophic co-activators that regulate a large body of transcription factors[1]. The mechanisms of transcriptional activation are not clear, but are likely to involve the associated histone acetyltransferase and kinase activities[13,14,15,16,17], together with interactions with additional accessory molecules[1,26]. In This report, we have characterised a new type of co-activator that acts in concert with p300 in the activation of transcription. JMY bears no obvious similarity to other known co-activators, including those involved with nuclear receptor activation[26,27,28,29], and thus likely represents a novel a class of co-activators. The protein sequence of JMY possesses a number of interesting characteristics, including homology to the adenovirus E1aCR2 motif and, although the significance of This has yet to be determined, it is noteworthy that the. interaction between JMY and p300 is sensitive to the action of adenovirus E1a.

Importantly, co-activation of p53 by JMY enhanced a specific physiological outcome, namely apoptosis, suggesting that JMY imparts an additional level of control in regulating the activity of p300/CBP responsive transcription factors. In contrast, p300 failed to effect the level of p53-dependent apoptosis, implying that JMY is an important effector molecule in directing the cellular response to p300. For p53, the additional control provided by JMY is a significant biological determinant in regulating the physiological outcome of transcriptional activation.

METHODS

Isolation of p300 interacting proteins.

The yeast strain CTY10.5 containing the LexA-β galactosidase reporter vector pLex (his) was as previously described[30]. pLex-p300$^{611-2283}$ was made by subcloning the NdeI fragment of p300 (3028 to 8046bp) into the SalI site of pLex (his). Screening a 10.5 d.p.c. mouse embryo random primed cDNA library fused to the VP16 trans activation domain[31] yielded a single positive clone containing 280bp of JMY sequence. Full length JMY cDNAs were isolated through a combined approach of screening cDNA libraries prepared from F9 EC[32] and PCC4 mouse teratocarcinoma (Stratagene) cells and RACE (Clontech).

Yeast two-hybrid interaction assays.

The yeast strain CTY10.5 and pLex-p300$^{611-2283}$ were as described above, and pGAD-E1a was constructed by subcloning the E1a 13S cDNA into pACTII (Clontech). CTY10.5 cells were transformed with the appropriate bait and prey vectors and assayed for β-galactosidase activity as described previously[30].

Transient transfection and reporter assays.

The activity of p(GRE)$_2$TATA-Cat (1.0 μg) was assayed in HeLa cells after transfection of the indicated amounts of p300 and JMY expression vectors (pCMV-p300 and pCMV-JMY). After transfection, cells were incubated in medium containing 10% dextran coated charcoal stripped serum with or without 0.5 μM dexamethasone for 24h, when cells were harvested and assayed for CAT activity. For transfection into SAOS2 cells, cells were incubated in 10% serum throughout and transfected with either pBax-luc[19] (2.0 μg) or pDHFR-luc[25] (1.0 μg) with either the expression vector for p53 (pCMV-p53; 0.25 μg) or E2F-1 (pCMV-E2F-1; 0.2 μg) respectively together with the indicated amounts of pCMV-p300 and PCMV-JMY and harvested 24–36h post transfection. All transfections were performed using the calcium phosphate procedure and included an-internal control pCMV-β-gal.

For the mammalian two-hybrid assay, 1 μg of pG4-p300$^{611\text{-}2283}$, pG4-p300$^{611\text{-}1257}$, -p300$^{1302\text{-}1572}$ or -p300$^{1572\text{-}2283}$ (ref. 9), were transfected with pVP16-JMY$^{469\text{-}558}$ into U2OS cells. The Gal4 reporter pG5-luc has been described previously[9].

Binding assays and immunoprecipitation.

Three regions of p300 were expressed as GST fusion proteins, namely GST-p300$^{1\text{-}596}$, -p300$^{744\text{-}1571}$ and -p300$^{1572\text{-}2370}$, as described[2]. Purified fusion proteins were incubated with in vitro translated JMY$^{335\text{-}588}$ or the E1a 13S polypeptide for 1h at 4° C. and then washed in 50mTris pH8.0, 150 mM NaCl and 0.1% NP40. The remaining bound protein proteins were separated on a 10% SDS-PAGE gel and detected by autoradioaugraphy. For immunoprecipitation, U2OS were transfected with expression vectors pG4-p300$^{611\text{-}2283}$, pG4, or pCMV-JMY (containing an HA epitope) by the calcium phosphate procedure. After 48h, cells were harvested in 50 mM Tris-HCl pH7.4, 60 mM NaCl, 5 mM EDTA, 0.5% NP40, 50 mM NaF, 1 mM DTT, 1 mM PMSF, 0.2 mM sodium orthovanedate, leupeptin (0.5 μg/ml), protease inhibitor (0.5 μg/ml), trypsin inhibitor (1.0 μg/ml) aprotinin (0.5 μg/ml) and bestatin (40 μg/ml) and incubated on ice for 30 min. The cell extract was pre-cleared by incubating with protein G agarose for 30 min at 4° C., and the supernatant immunoprecipitated with anti-mouse Gal4 monoclonal antibody (Santa-Cruz) which was harvested with protein-A agarose. The agarose beads were collected and washed three times in the extraction buffer before denaturation and SDS-polyacrylamide (7.5%) gel electrophoresis. Immunoblotting was subsequently performed with an anti-mouse HA monoclonal antibody (Boehringer Mannheim) or an anti-peptide rabbit antibody against a peptide taken from JMY.

Immunofluorescence and apoptosis assays.

SAOS2 cells, grown in 10% foetal calf serum, were transfected with pCMV-p53 (3 μg) either alone or together with pCMV-JMY (5 μg), pCMV-p300 (5 μg) or both. After 14h incubation, cells were washed and further incubated for 24h in the presence of 0.2% serum. Cells were fixed in 4% paraformaldehyde at 4° C. for 20 min, rinsed and permeabilised in PBS containing 0.2% Triton X-100 at 4° C. for 10 min. Subsequently, calls were treated with the anti-p53 monoclonal antibody 421, washed and further incubated in tetramethylrhodamine-conjugated goat anti-mouse (Southern Biotechnology Associates, Inc.) for 2h at room temperature. For the TUNEL (TdT-mediated dUTP nick end labelling) analysis, cells were incubated in a $Ca^{2+}$reaction buffer containing fluorescein-dUTP and dNTP, and terminal deoxynucleotidyl transferase (Boehringer Mannheim) at 37° C. for 1h. For DAPI (4', 6-diamidine-2-phenylindole) staining, cells were incubated with DAPI (0.2 μg/ml) in PBS at room temperature for 2 min. Coverslips were washed three times in PBS, mounted and viewed.

REFERENCES

1. Shikama, N., et al. Trends Cell Biol. 7, 230–236 (1997).
2. Arany, Z., et al. Nature 374, 81–84 (1995).
3. Lundblad, J. R., et al. Nature 374, 85–88 (1995).
4. Eckner, R., et al. Genes Dev. 8, 869–884 (1994).
5. Eckner, R., et al. Genes Dev. 10, 2478–2490 (1996).
6. Puri, P. L., et al. EMBO J. 16, 369–383 (1997).
7. Lill, N. L., et al. Nature 387, 823–827 (1997).
8. Gu, W., et al. Nature 387, 819–822 (1997).
9. Lee, C-W., Sorensen, T. S., Shikama, N. and La Thangue, N. B. Functional interplay between p53 and E2F through co-activator p300; Submitted.
10. Avantaggiati, M. L., et al. EMBO J. 15, 2236–2248 (1996).
11. Borrow, J., et al. Nature Genetics 14, 33–41 (1996).
12. Muraoka, M., et al. Oncogene 12, 1565–1569 (1996).
13. Yang, X-J., et al. Nature 382, 319–324 (1996).
14. Bannister, A. J. and Kouzarides, T. Nature 384, 641–643 (1996).
15. Ogryzko, V. V., et al. Cell 87, 953–959 (1996).
16. Perkins, N. D., et al. Science 275, 523–527 (1997).
17. Gu, W. and Roeder, R. G. Cell 90, 595–606 (1997).
18. Ko, L-J. and Prives,C. Genes Dev. 10, 1054–1072 (1996).
19. Miyashita, T. and Reed, J. C. Cell 80, 293–299 (1995).
20. Sabbatini, P., et al. Genes Dev. 9, 2184–2192 (1995).
21. Crook, T., et al. Cell 79, 817–827 (1994).
22. El-Deiry, et al. Cell 75, 817–825 (1993).
23. Chen, X., et al. Genes Dev. 10, 2438–2451 (1996).
24. Chakravarti, D., et al. Nature 383, 99–103 (1996).
25. Sorensen, T. S., et al. Mol. Cell. Biol. 16, 5888–5895 (1996).
26. Glass, C. K., et al. Current Opinion in Cell Biology 9, 222–232 (1997).
27. Torchia, J., et al. Nature 387, 677–684 (1997).
28. Chen, H., et al. Cell 90, 569–580 (1997).
29. Li, H., et al. Proc. Natl, Acad, Sci, USA. 94, 8479–8484
30. Buck, V., et al. Oncogene 11, 31–38 (1995).
31. Vojtek, A. B., et al. Cell 74, 205–214 (1993).
32. Girling, R., et al. Nature 362, 83–87 (1993).
33. Onate SA et al. Science 270: 1354–1357 (1997)
34. Neuman E et al. Mol. Cell. Biol 17 (9): 5338–5347 (1997)
35. Zwijsen RML et al. Cell 88, 405–415 (1997)
36. Xiong Y et al. Cell 65(4): 691–699 (1991)
37. Greene GL et al. Science 231 (4742): 1150–1154 (1996)
38. Hanstein B et al. Proc Natl Acad Sci USA 93 (21): 11540–11545 (1996)
39. Sadovsky et al., 1995, Mol Cell Biol 15, 1554–1563)

What is claimed is:

1. An isolated nucleic acid comprising a polynucleotide encoding a polypeptide of SEQ ID NO:2, or its complement.

2. The isolated nucleic acid of claim 1 comprising nucleotides 127 to 3075 of SEQ ID NO:1.

3. A vector comprising a nucleic acid according to claim 1 operably linked to a promoter heterologous to said nucleic acid.

4. A vector comprising a nucleic acid according to claim 2 operably linked to a promoter heterologous to said nucleic acid.

5. A host cell comprising a vector according to claim 3, the promoter of said vector being compatible with the host cell.

6. A host cell comprising a vector according to claim 4, the promoter of said vector being compatible with the host cell.

* * * * *